United States Patent
Nirogi et al.

(10) Patent No.: US 9,079,888 B2
(45) Date of Patent: Jul. 14, 2015

(54) COMPOUNDS AS HISTAMINE H3 RECEPTOR LIGANDS

(75) Inventors: Ramakrishna Nirogi, Hyderabad (IN); Anil Karbhari Shinde, Hyderabad (IN); Ramasastri Kambhampati, Hyderabad (IN); Amol Dinakar Deshpande, Hyderabad (IN); Adi Reddy Dwarampudi, Hyderabad (IN); Narasimhareddy Gangadasari, Hyderabad (IN); Sangram Keshari Saraf, Hyderabad (IN); Vishwottam Nagaraj Kandikere, Hyderabad (IN); Pradeep Jayarajan, Hyderabad (IN); Ishtiyaque Ahmad, Hyderabad (IN); Mohmadsadik Abdulhamid Mulla, Hyderabad (IN); Venkateswarlu Jasti, Hyderabad (IN)

(73) Assignee: Suven Life Sciences Limited, Hyderabad (IN)

( * ) Notice: Subject to any disclaimer, the term of this patent is extended or adjusted under 35 U.S.C. 154(b) by 139 days.

(21) Appl. No.: 14/000,362

(22) PCT Filed: Jun. 7, 2011

(86) PCT No.: PCT/IN2011/000380
§ 371 (c)(1),
(2), (4) Date: Nov. 25, 2013

(87) PCT Pub. No.: WO2012/114348
PCT Pub. Date: Aug. 30, 2012

(65) Prior Publication Data
US 2014/0135304 A1    May 15, 2014

(30) Foreign Application Priority Data
Feb. 23, 2011   (IN) .............................. 520/CHE/2011

(51) Int. Cl.
| | | |
|---|---|---|
| *C07D 401/12* | (2006.01) | |
| *C07D 405/12* | (2006.01) | |
| *C07D 413/12* | (2006.01) | |
| *C07D 401/14* | (2006.01) | |
| *C07D 211/46* | (2006.01) | |

(52) U.S. Cl.
CPC ............ *C07D 401/14* (2013.01); *C07D 211/46* (2013.01); *C07D 401/12* (2013.01); *C07D 405/12* (2013.01); *C07D 413/12* (2013.01)

(58) Field of Classification Search
CPC .. C07D 401/12; C07D 405/12; C07D 401/14; C07D 413/12
See application file for complete search history.

(56) References Cited

U.S. PATENT DOCUMENTS

| | | |
|---|---|---|
| 2009/0170869 A1 | 7/2009 | Best |
| 2010/0029608 A1 | 2/2010 | Finley |
| 2010/0048580 A1 | 2/2010 | Beavers |

FOREIGN PATENT DOCUMENTS

| | | |
|---|---|---|
| WO | 2009100120 | 8/2009 |
| WO | 2009121812 | 10/2009 |
| WO | 2009135842 | 11/2009 |
| WO | 2010045306 | 4/2010 |

OTHER PUBLICATIONS

European Patent Office, "International Search Report" and "Written Opinion" issued Oct. 21, 2011 in Application No. PCT/IN2011/000380.
European Patent Office, "International Preliminary Report on Patentability" issued Jan. 14, 2013 in Application No. PCT/IN2011/000380.
Esbenshade et al., "The histamine H3 receptor: an attractive target for the treatment of cognitive disorders" Br. J. Pharmacol. 154:1166-81 (2008).
Chazot, "Therapeutic Potential of Histamine H3 Receptor Antagonists in Dementias" Drug News & Perspect. 23 (2):99-103 (2010).
Vohora et al., "Histaminergic H3-Receptors as Modulators of CNS Function" Indian J. Pharmacol. 33:17-28 (2001).
Ligneau et al., "Brain histamine and schizophrenia: Potential therapeutic applications of H3-receptor inverse agonists studied with BF2.649" Biochem Pharmacol. 73:1215-24 (2007).
Medhurst et al., "Novel histamine H3 receptor antagonists GSK 189254 and GSK 334429 are efficacious in surgically-induced and virally-induced rat models of neuropathic pain" Pain 138:61-69 (2008).
Crow, "Investigational drugs for eating disorders" Expert Opin. Investig. Drugs 6(4):427-36 (1997)—Abstract.
Ennaceur, A., Delacour, J., "A new one-trial test for neurobiological studies of memory in rats—Behavioural data" Behav. Brain Res. 31:47-59 (1988).
Crow, Scott, "Investigational drugs for eating disorders", Expert Opin. Investig. Drugs 6(4):427-36 (1997), Ashley Publications Ltd.

Primary Examiner — Rebecca Anderson
(74) Attorney, Agent, or Firm — IpHorgan Ltd.

(57) ABSTRACT

The present invention relates to novel compounds of formula (I), and their pharmaceutically acceptable salts and compositions containing them.

(I)

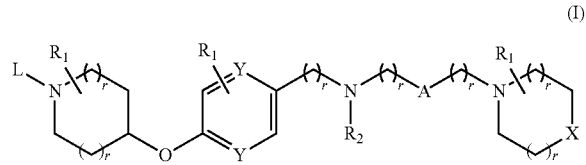

The present invention also relates to a process for the preparation of above compounds of formula (I), and their pharmaceutically acceptable salts.
The compounds of formula (I) are useful in the treatment of various disorders that are related to Histamine $H_3$ receptors.

15 Claims, No Drawings

COMPOUNDS AS HISTAMINE H3 RECEPTOR LIGANDS

CROSS REFERENCE TO RELATED APPLICATIONS

This application is a national stage completion of PCT Application No. PCT/IN2011/000380, filed Jun. 7, 2011, and claims the benefit of Indian Application No. 520/CHE/2011, filed Feb. 23, 2011. Each of these applications, numbers PCT/IN2011/000380 and 520/CHE/2011, is incorporated by reference herein in its entirety.

FIELD OF INVENTION

The present invention relates to novel compounds of formula (I) and their pharmaceutically acceptable salts and compositions containing them, for treatment of various disorders that are related to Histamine $H_3$ receptors.

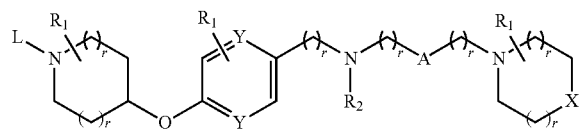

(I)

BACKGROUND OF THE INVENTION

Histamine H3 receptor is a G-protein coupled receptor (GPCR) and one out of the four receptors of Histamine family. Histamine H3 receptor is identified in 1983 and its cloning and characterization were done in 1999. Histamine $H_3$ receptor is expressed to a larger extent in central nervous system and lesser extent in the peripheral nervous system.

Literature evidence suggests that Histamine H3 receptors can be used in treatment of cognitive disorders (British Journal of Pharmacology, 2008, 154(6), 1166-1181), dementia (Drug News Perspective, 2010, 23(2), 99-103), attention deficit hyperactivity disorder, epilepsy, sleep disorders, sleep apnea, obesity (Indian Journal of Pharmacology, 2001, 33, 17-28), schizophrenia (Biochemical Pharmacology, 2007, 73(8), 1215-1224), eating disorders (Investigational drugs for eating disorders, 1997, 6(4), 427-436) and pain (Pain, 2008, 138(1), 61-69).

Patent publications US 2009/0170869, US 2010/0029608, US 2010/0048580, WO 2009/100120, WO 2009/121812 and WO 2009/135842 disclosed series of compounds as ligands at Histamine H3 receptors. While some Histamine H3 receptor ligands have been disclosed, no compound till date is launched in market in this area of research, and there still exists a need and scope to discover new drugs with novel chemical structures for treatment of disorders affected by Histamine H3 receptors.

SUMMARY OF THE INVENTION

The present invention relates to novel Histamine $H_3$ receptor ligand compounds of the formula (I),

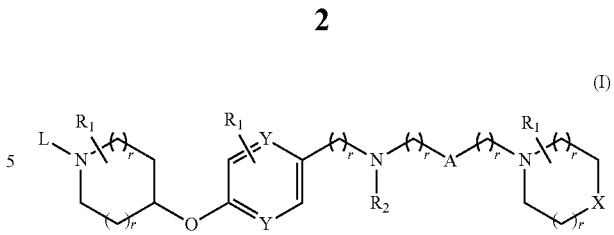

(I)

wherein,
at each occurrence, $R_1$ is independently selected from hydrogen, hydroxy, hydroxyalkyl, halogen, alkyl, alkoxy, haloalkyl, haloalkoxy, cyano or —C(O)—$NH_2$
L is alkyl or

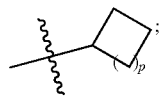

X is C, O or N—$R_2$;
Y is C or N;
A is —C(O)— or —$CH_2$;
$R_2$ is hydrogen, alkyl, —C(O)-alkyl or —S(O)$_2$-alkyl;
"r" is an integer ranging from 0 to 1;
"p" is an integer ranging from 0 to 3; or a pharmaceutically acceptable salt thereof.

The present invention relates to use of a therapeutically effective amount of compound of formula (I), to manufacture a medicament in the treatment of various disorders that are related to Histamine H3 receptors.

Specifically, the compounds of this invention are useful in the treatment of various disorders such as cognitive disorders, dementia, attention deficit hyperactivity disorder, schizophrenia, epilepsy, sleep disorders, sleep apnea, obesity, eating disorders and pain.

In another aspect, the invention relates to pharmaceutical compositions containing a therapeutically effective amount of at least one compound of formula (I), and their pharmaceutically acceptable salts thereof, in admixture with pharmaceutical acceptable excipient.

In still another aspect, the invention relates to methods for using compounds of formula (I).

In yet another aspect, the invention further relates to the process for preparing compounds of formula (I) and their pharmaceutically acceptable salts.

Representative compounds of the present invention include those specified below and their pharmaceutically acceptable salts. The present invention should not be construed to be limited to them.

N-[4-(1-Cyclobutyl piperidin-4-yloxy)phenyl]-2-(morpholin-4-yl)acetamide dihydrochloride;
2-[4-(1-Cyclobutyl piperidin-4-yloxy)phenylamino]-1-(morpholin-4-yl)ethanone hydrochloride;
N-[4-(1-Cyclobutyl piperidin-4-yloxy)-2-fluoro-phenyl]-2-(morpholin-4-yl)acetamide dihydrochloride;
N-[4-(1-Cyclobutyl piperidin-4-yloxy)benzyl]morpholine-4-yl amide;
N-[4-(1-Cyclobutyl piperidin-4-yloxy)-3-fluoro phenyl]-2-(morpholin-4-yl)acetamide;
N-[4-(1-Cyclobutyl piperidin-4-yloxy)-2-methyl phenyl]-2-(3,3-difluoro pyrrolidin-1-yl) acetamide;
N-[4-(1-Cyclobutyl piperidin-4-yloxy)-2-trifluoromethyl phenyl]-2-(piperidin-1-yl)acetamide;
N-[4-(1-Cyclopentyl piperidin-4-yloxy)phenyl]-2-(morpholin-4-yl)acetamide;

N-[4-(1-Cyclobutyl piperidin-4-yloxy)-2-trifluoromethyl phenyl]-2-(morpholin-4-yl)acetamide;
N-[4-(1-Isopropyl piperidin-4-yloxy)-2-methyl-phenyl]-2-(pyrrolidin-1-yl)acetamide;
N-[4-(1-Cyclobutyl piperidin-4-yloxy)-2-methyl phenyl]-2-(pyrrolidin-1-yl)acetamide;
N-[4-(1-Cyclopentyl piperidin-4-yloxy)-2-methyl phenyl]-2-(piperidin-1-yl)acetamide;
N-[4-(1-Cyclobutyl piperidin-4-yloxy)-2-methyl phenyl]-2-(piperidin-1-yl)acetamide;
N-[4-(1-Cyclobutyl piperidin-4-yloxy)phenyl]-N-methyl-2-(morpholin-4-yl)acetamide;
N-[4-(1-Cyclopentyl piperidin-4-yloxy)-2-methyl phenyl]-2-(R-2-methylpyrrolidin-1-yl) acetamide;
N-[4-(1-Cyclobutyl piperidin-4-yloxy)-2-methyl phenyl]-2-(R-2-methylpyrrolidin-1-yl) acetamide;
N-[4-(1-Cyclobutyl piperidin-4-yloxy)-2-methoxy phenyl]-2-(morpholin-4-yl)acetamide;
N-[4-(1-Cyclobutyl piperidin-4-yloxy)-2-trifluoromethyl phenyl]-2-(4-hydroxy piperidin-1-yl) acetamide;
N-[4-(1-Cyclobutyl piperidin-4-yloxy)phenyl]-2-(4-hydroxy piperidin-1-yl)acetamide;
N-[4-(1-Cyclopentyl piperidin-4-yloxy)-2-fluoro phenyl]-2-(morpholin-4-yl)acetamide dihydrochloride;
N-[4-(1-Cyclobutyl piperidin-4-yloxy)phenyl]-2-(pyrrolidin-1-yl)acetamide;
N-[4-(1-Isopropyl piperidin-4-yloxy)phenyl]-2-(morpholin-4-yl)acetamide;
N-[4-(1-Cyclopropyl piperidin-4-yloxy)phenyl]-2-(morpholin-4-yl)acetamide;
N-[4-(1-Cyclobutyl piperidin-4-yloxy)phenyl]-2-(4-isopropyl[1,4]diazepan-1-yl)acetamide;
N-[4-(1-Cyclobutyl piperidin-4-yloxy)phenyl]-2-(2-hydroxymethyl morpholin-4-yl)acetamide;
N-[4-(1-Cyclobutyl piperidin-4-yloxy)phenyl]-3-(morpholin-4-yl)propionamide;
N-[4-(1-Cyclopentyl piperidin-4-yloxy)phenyl]-2-(piperidin-1-yl)acetamide dihydrochloride;
N-[4-(1-Cyclopentyl piperidin-4-yloxy)phenyl]-2-(pyrrolidin-1-yl)acetamide dihydrochloride;
N-[4-(1-Cyclobutyl piperidin-4-yloxy)phenyl]-2-(piperidin-1-yl)acetamide;
N-[4-(1-Cyclobutyl piperidin-4-yloxy)-2-trifluoromethyl phenyl]-2-(pyrrolidin-1-yl)acetamide dihydrochloride;
N-[4-(1-Cyclobutyl piperidin-4-yloxy)phenyl]-N-(2-morpholin-4-yl ethyl)acetamide;
[4-(1-Cyclobutyl piperidin-4-yloxy)phenyl]-(2-morpholin-4-yl ethyl)amine;
N-[4-(1-Cyclobutyl piperidin-4-yloxy)phenyl]-2-(R-2-hydroxymethylpyrrolidin-1-yl)acetamide L(+) tartarate;
N-[2-(1-Cyclobutyl piperidin-4-yloxy)pyridin-5-yl]-N-[2-(morpholin-4-yl)ethyl]acetamide;
N-[2-(1-Cyclobutyl piperidin-4-yloxy)pyridin-5-yl]-2-(piperidin-1-yl)acetamide;
N-[2-(1-Cyclobutyl piperidin-4-yloxy)pyridin-5-yl]-2-(morpholin-4-yl)acetamide;
N-[4-(1-Cyclobutyl piperidin-4-yloxy)-2-fluoro phenyl]-N-[2-(morpholin-4-yl)ethyl]acetamide;
N-[4-(1-Cyclopropyl piperidin-4-yloxy)phenyl]-N-[2-(morpholin-4-yl)ethyl]acetamide L(+) tartarate;
N-[4-(1-Cyclobutyl piperidin-4-yloxy)phenyl]-2-(1-acetyl piperazin-4-yl)acetamide dihydrochloride;
N-[4-(1-Cyclobutyl piperidin-4-yloxy)-2-methyl phenyl]-2-(4-hydroxy piperidine-1-yl) acetamide;
N-[4-(1-Cyclopropyl piperidin-4-yloxy)phenyl]-2-(R-2-hydroxymethylpyrrolidin-1-yl) acetamide;
N-[4-(1-Cyclobutyl piperidin-4-yloxy)benzyl]-2-(morpholin-4-yl)acetamide;
N-[4-(1-Cyclobutyl piperidin-4-yloxy)-2-fluoro benzyl]-2-(morpholin-4-yl)acetamide;
N-[4-(1-Cyclobutyl piperidin-4-yloxy)phenyl]-2-(3-hydroxy azetidin-1-yl)acetamide;
N-[4-(1-Cyclobutyl piperidin-4-yloxy)-2-fluoro phenyl]-2-(3-methoxy azetidin-1-yl)acetamide;
N-[4-(1-Cyclobutyl piperidin-4-yloxy)-2-fluoro phenyl]-2-(2-hydroxymethylpyrrolidin-1-yl) acetamide;
N-[2-Chloro-4-(1-cyclobutyl piperidin-4-yloxy)phenyl]-2-(morpholin-4-yl)acetamide;
N-[2-Chloro-4-(1-cyclobutyl piperidin-4-yloxy)phenyl]-2-(piperidin-1-yl)acetamide;
N-[4-(1-Cyclobutyl piperidin-4-yloxy)phenyl]-2-(tetrahydro pyran-4-yloxy)acetamide;
2-[4-(1-Cyclobutyl piperidin-4-yloxy)-2-fluoro phenylamino]-1-(morpholin-4-yl)ethanone; and
N-[4-(1-Cyclobutyl piperidin-4-yloxy)-2-fluoro phenyl]-N-(2-morpholin-4-yl ethyl)acetamide;

DETAILED DESCRIPTION OF THE INVENTION

Unless otherwise stated, the following terms used in the specification and claims have the meanings given below:

The term "halogen" means fluorine, chlorine, bromine or iodine.

The term "alkyl" means straight chain or branched hydrocarbon radical consisting solely of carbon and hydrogen atoms, containing no unsaturation, having from one to eight carbon atoms, and which is attached to the rest of the molecule by a single bond. Exemplary "alkyl" groups include methyl, ethyl, n-propyl, iso-propyl and the like.

The term "alkoxy" means an alkyl group attached via an oxygen linkage to the rest of the molecule. Exemplary "alkoxy" groups include methoxy, ethoxy, propyloxy, iso-propyloxy and the like.

The term "haloalkyl" means straight or branched chain alkyl radicals containing one to three carbon atoms. Exemplary "haloalkyl" groups include fluoromethyl, difluoromethyl, trifluoromethyl, trifluoroethyl, fluoroethyl, difluoroethyl and the like.

The term "haloalkoxy" means straight or branched chain alkoxy radicals containing one to three carbon atoms. Exemplary "haloalkoxy" groups include fluoromethoxy, difluoromethoxy, trifluoromethoxy, trifluoroethoxy, fluoroethoxy, difluoroethoxy and the like.

The term "hydroxyalkyl" means hydroxy group is directly bonded to alkyl chain. Exemplary "hydroxyalkyl" groups include hydroxymethyl, hydroxyethyl and the like.

The terms "treating", "treat" or "treatment" embrace all the meanings such as preventative, prophylactic and palliative.

The phrase "pharmaceutically acceptable salts" indicates that the substance or composition must be compatible chemically and/or toxicologically, with the other ingredients comprising a formulation, the mammal being treated therewith.

The phrase "therapeutically effective amount" is defined as 'an amount of a compound of the present invention that (i) treats or prevents the particular disease, condition or disorder (ii) attenuates, ameliorates or eliminates one or more symptoms of the particular disease, condition or disorder (iii) prevents or delays the onset of one or more symptoms of the particular disease, condition or disorder described herein.

Commercial reagents were utilized without further purification. Room temperature refers to 25-40° C. Unless otherwise stated, all mass spectra were carried out using ESI conditions. $^1$H-NMR spectra were recorded at 400 MHz on a Bruker instrument. Deuterated chloroform, methanol or dimethylsulfoxide was used as solvent. TMS was used as internal reference standard. Chemical shift values are expressed in parts per million (δ) values. The following abbreviations are used for the multiplicity for the NMR signals: s=singlet, bs=broad singlet, d=doublet, t=triplet, q=quartet, qui=quintet, h=heptet, dd=double doublet, dt=double triplet, tt=triplet of triplets, m=multiplet. Chromatography refers to column chromatography performed using 100-200 mesh silica gel and executed under nitrogen pressure (flash chromatography) conditions.

Pharmaceutical Compositions

In order to use the compounds of formula (I) in therapy, they will normally be formulated into a pharmaceutical composition in accordance with standard pharmaceutical practice.

The pharmaceutical compositions of the present invention may be formulated in a conventional manner using one or more pharmaceutically acceptable excipient. The pharmaceutically acceptable excipient is carrier or diluent. Thus, the active compounds of the invention may be formulated for oral, intranasal or parenteral (e.g., intravenous, intramuscular or subcutaneous). Such pharmaceutical compositions and processes for preparing same are well known in the art (The Science and Practice of Pharmacy, D. B. Troy, 21st Edition, Williams & Wilkins, 2006).

The dose of the active compounds can vary depending on factors such as the route of administration, age and weight of patient, nature and severity of the disease to be treated and similar factors. Therefore, any reference herein to a pharmacologically effective amount of the compounds of general formula (I) refers to the aforementioned factors. A proposed dose of the active compounds of this invention, for either oral or parenteral administration, to an average adult human, for the treatment of the conditions referred above.

Methods of Preparation

The compounds of formula (I) can be prepared by Scheme I as shown below.

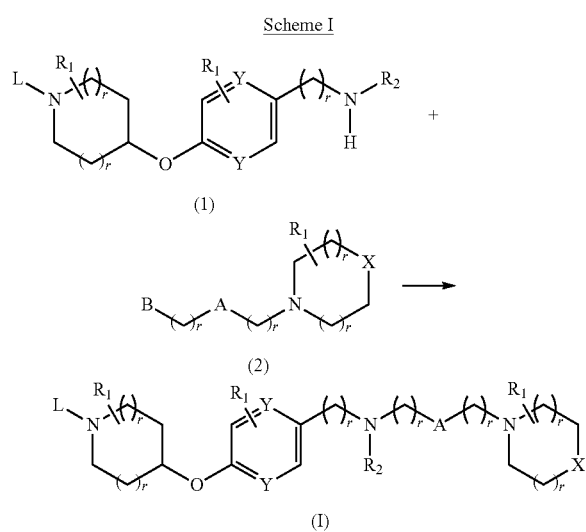

In above Scheme I, B is OH, Cl or Br; and all other symbols are as defined above.

The compound of formula (I) is coupled with compound of formula (2) to form compound of formula (I). This reaction is preferably carried out in solvent such as tetrahydrofuran, toluene, ethyl acetate, dichloromethane, dimethylformamide, and the like or a mixture thereof and preferably by using dichloromethane and dimethylformamide. The reaction may be carried out in the presence of a base such as sodium hydride, sodium carbonate, potassium carbonate, diisopropylethylamine, sodium bicarbonate, sodium hydroxide or mixtures thereof and preferably by using potassium carbonate and diisopropylethylamine. The reaction may be affected in the presence of a coupling agent such as O-(Benzotriazol-1-yl)-N,N,N',N'-tetramethyluronium tetrafluoroborate. The reaction is carried out at temperature of 25° C. to 85° C. based on choice of solvent and base. The duration of the reaction may range from 4 to 18 hours, preferably from a period of 10 to 14 hours.

The compounds of formula (1) and formula (2) may be commercially available or can be prepared by conventional methods or by modification, using known process.

The compounds of formula (I) can also be prepared by using Scheme II as shown below

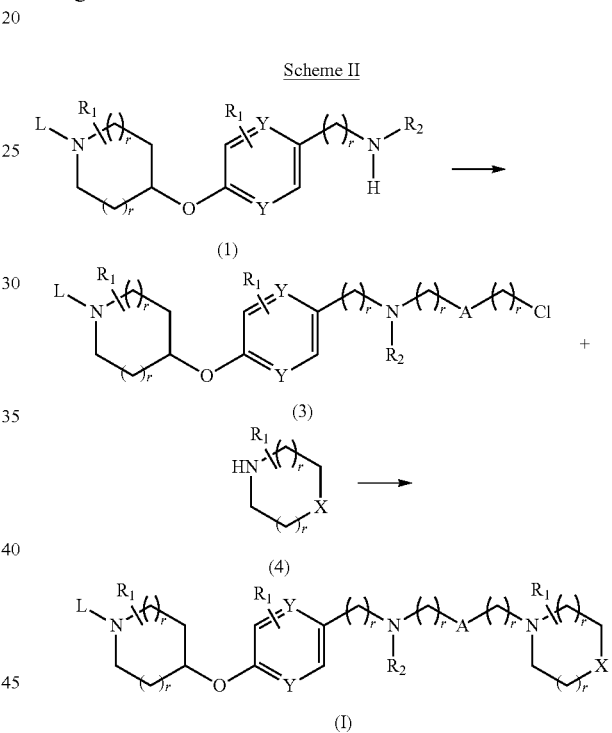

In above Scheme II, all symbols are as defined above.

The compound of formula (1) is converted to compound of formula (3). The compound of formula (3) is coupled with compound of formula (4) to form compound of formula (I).

In the first step of the above preparation, the compound of formula (1) is converted to compound of formula (3). This reaction is preferably carried out in solvent such as tetrahydrofuran, toluene, ethyl acetate, dichloromethane, dimethylformamide, and the like or a mixture thereof and preferably by using dichloromethane. The reaction may be affected in the presence of a base such as triethylamine, potassium carbonate, diisopropylethylamine, pyridine and the like or a mixture thereof and preferable by using triethylamine. The reaction is carried out at temperature of −10° C. to 10° C. based on choice of solvent and base. The duration of the reaction may range from 0.5 to 2 hours, preferably from a period of 45 minutes to 1.5 hours.

In the second step of the above preparation, the compound of formula (3) is coupled with compound of formula (4) to form compound of formula (I). This reaction is preferably carried out in solvent such as tetrahydrofuran, acetonitrile, toluene, ethyl acetate, dichloromethane, dimethylformamide, and the like or a mixture thereof and preferably by using acetonitrile. The reaction may be affected in the presence of a base such as triethylamine, potassium carbonate, diisopropylethylamine, pyridine and the like or a mixture thereof and preferable by using potassium carbonate. The reaction is carried out at temperature of 25° C. to 85° C. based on choice of solvent and base. The duration of the reaction may range from 3 to 7 hours, preferably from a period of 4 to 6 hours.

The compounds of formula (1) and formula (4) may be commercially available or can be prepared by conventional methods or by modification, using known process.

The compounds of formula (I) can also be prepared by using Scheme III as shown below

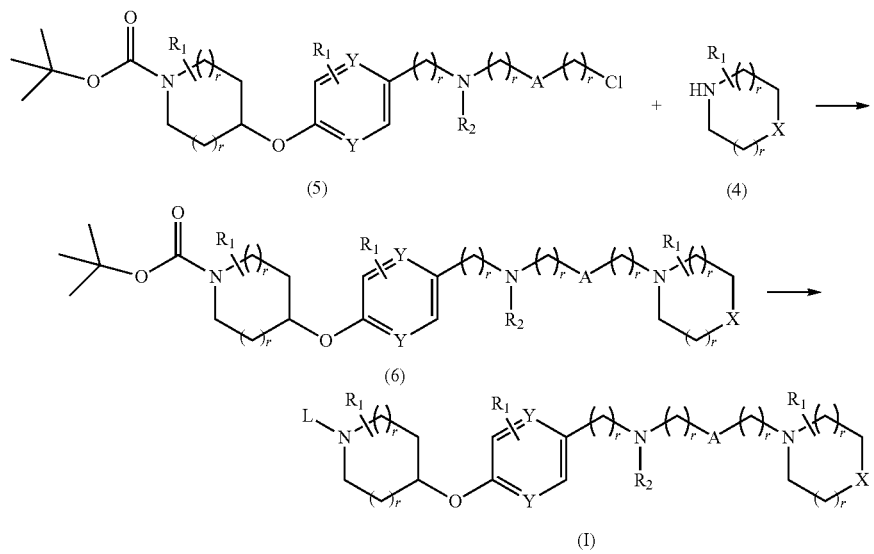

Scheme III (5)

(4)

(6)

(I)

In above Scheme III, all symbols are as defined above.

The compound of formula (5) is coupled with compound of formula (4) to form compound formula (6). The compound of formula (6) is converted to compound of formula (I).

In the first step of the above preparation, the compound of formula (5) is coupled with compound of formula (4) to form compound of formula (6). This reaction is preferably carried out in solvent such as acetonitrile, tetrahydrofuran, toluene, ethyl acetate, dichloromethane, dimethylformamide, and the like or a mixture thereof and preferably by using acetonitrile. The reaction may be affected in the presence of a base such as triethylamine, potassium carbonate, diisopropylethylamine, pyridine and the like or a mixture thereof and preferable by using potassium carbonate. The reaction is carried out at temperature of 25° C. to 70° C. based on choice of solvent and base. The duration of the reaction may range from 3 to 7 hours, preferably from a period of 4 to 6 hours.

In the second step of the above preparation, the compound of formula (6) is subjected to deprotection followed by reductive cycloalkylation to form compound of formula (I). The deprotection reaction is preferably carried out in solvent such as acetonitrile, tetrahydrofuran, toluene, ethyl acetate, dichloromethane, dimethylformamide, methanol, ethanol, isopropanol and the like or a mixture thereof and preferably by using alcoholic solvent or dichloromethane. The reaction may be affected in the presence of an acid such as trifluoroacetic acid, sulfuric acid, acetic acid, perchloric acid, hydrochloric acid, and the like or a mixture thereof and preferable by using trifluoroacetic acid. The reaction is carried out at 25° C. to 60° C. The duration of the reaction may range from 4 to 10 hours, preferably from a period of 4 to 8 hours. After deprotection the isolated base is treated with a carbonyl compound like acetone, cyclobutanone or cyclopentanone in presence of solvent such as tetrahydrofuran, aceticacid, dichloromethane, dichloroethane and the like or a mixture thereof and preferably by using dichloroethane in presence of acetic acid. The reaction is effected in presence of a reducing agent such as sodium triacetoxy borohydride, sodium cyanoborohydride, lithium aluminium hydride, sodium borohydride and the like or a mixture thereof and preferably by using sodium triacetoxyborohydride. The reaction is carried out at temperature of 10° C. to 40° C. The duration of the reaction may range from 4 to 16 hours.

The compounds of formula (4) and formula (5) may be commercially available or can be prepared by conventional methods or by modification, using known process.

If necessary, any one or more than one of the following steps can be carried out,
i) converting a compound of the formula (I) into another compound of the formula (I) or ii) forming a pharmaceutically acceptable salt.

Process (i) may be performed by further chemical modifications using well known reactions such as oxidation, reduction, protection, deprotection, rearrangement, halogenation, hydroxylation, alkylation, alkylthiolation, demethylation, O-alkylation, O-acylation, N-alkylation, N-alkenylation, N-acylation, N-cyanation, N-sulfonylation, coupling and the like.

In process (ii) pharmaceutically acceptable salts may be prepared conventionally by reaction with the appropriate acid or acid derivative.

Suitable pharmaceutically acceptable salts will be apparent to those skilled in the art and include those described in J. Pharm. Sci., 1977, 66, 1-19, such as acid addition salts formed with inorganic acids like hydrochloric, hydrobromic, sulfuric, nitric or phosphoric acid and organic acids like succinic, maleic, acetic, fumaric, citric, malic, tartaric, benzoic, p-toluic, p-toluenesulfonic, methanesulfonic or benzenesulfonic acid.

EXAMPLES

The novel compounds of the present invention were prepared according to the following experimental procedures, using appropriate materials and appropriate conditions.

Preparation 1: Preparation of
4[(1-Cyclobutyl-4-piperidinyl)oxy]aniline

Step (i): Preparation of 1-Cyclobutyl-4-piperidinol

A solution of 4-piperidinol (80 g, 0.792 moles) and cyclobutanone (67.2 g, 0.96 moles) in ethylene dichloride (1 L) was treated with sodium triacetoxyborohydride (251.1 g, 1.184 moles) portion wise and the mixture was stirred at room temperature for 5 hours. The reaction mixture was quenched in chilled water (1 L) and the resulting mass was basified with lye solution. The layers were separated, and the aqueous layer was extracted with dichloromethane (2×500 mL). The combined organic layers were washed with water, dried over sodium sulfate and concentrated to afford the title compound 100 g (Yield: 81.46%).

$^1$H-NMR (δ ppm): 1.55-2.02 (13H, m), 2.64-2.74 (2H, m), 3.68-3.70 (1H, m);

Mass (m/z): 155.9 (M+H)$^+$.

Step (ii): Preparation of
1-Cyclobutyl-4-(4-nitrophenoxy)piperidine

To a stirred solution of sodium hydride (24.76 g, 60% in mineral oil, 0.619 moles) in dimethylformamide (100 mL) was added 1-cyclobutyl-4-piperidinol (80 g, 0.516 moles, obtained in the above step) in dimethylformamide (300 mL) at 10° C. under a nitrogen atmosphere. The mass was stirred for 1 hour. A solution of 4-fluoronitrobenzene (87.3 g, 0.619 moles) in dimethylformamide (300 mL) was added drop wise to the above reaction mass at room temperature. After completion of reaction, the mass was quenched on to chilled water (2 L) and stirred for 1 hour. The obtained solids were separated and dissolved in ethyl acetate (1 L). The resulting ethyl acetate layer was washed with water, dried over sodium sulfate and concentrated under vacuum. The residue, thus obtained, was purified by flash chromatography (methanol: chloroform, 2:8) to afford the title compound 99.7 g (Yield: 70%).

$^1$H-NMR (δ ppm): 1.67-1.71 (2H, m), 1.83-1.91 (4H, m), 2.00-2.08 (4H, m), 2.11-2.19 (2H, m), 2.51-2.60 (2H, m), 2.71-2.78 (1H, m), 4.44-4.46 (1H, m), 6.93-6.95 (2H, d, J° 9.2 Hz), 8.17-8.20 (2H, d, J=9.2 Hz);

Mass (m/z): 277.3 (M+H)$^+$.

Step (iii): Preparation of
4[(1-Cyclobutyl-4-piperidinyl)oxy]aniline

Hydrogen gas was bubbled through a solution of 1-Cyclobutyl-4-(4-nitrophenoxy)piperidine (94.9 g, 0.344 moles, obtained in above step) over 10% Pd/C (95 g) in methanol (2 L) at room temperature, for 5 hours. The mixture was filtered through a pad of celite, and the filtrate was concentrated under vacuum to obtain the title compound 81 g (Yield: 95.7%).

$^1$H NMR (δ ppm): 1.62-2.07 (12H, m), 2.62-2.76 (3H, m), 3.43-3.47 (2H, m), 4.13-4.17 (1H, m), 6.61-6.63 (2H, d, J=8.7 Hz), 6.75-6.77 (2H, d, J=8.7 Hz);

Mass (m/z): 247.5 (M+H)$^+$.

Preparation 2: Preparation of 4-(1-Cyclobutyl piperidin-4-yloxy)benzylamine

Step (i): Preparation of 4-(4-Cyano phenoxy)piperidine-1-carboxylic acid tert-butyl ester A solution of 4-hydroxy benzonitrile (15 g, 0.126 moles), potassium carbonate (28.89 g, 0.208 moles) and 4-(Toluene-4-sulfonyloxy)piperidine-1-carboxylic acid tert-butyl ester (57.62 g, 0.162 moles) in dimethylformamide (150 mL) was stirred at 100° C. while monitoring the progress of the reaction by thin layer chromatography. After completion of reaction, the reaction mass was quenched on to water (400 mL) and extracted with ethyl acetate (3×300 mL). The resulting ethyl acetate layer was washed with brine solution, dried over sodium sulfate and concentrated under reduced pressure to obtain the crude residue, which was further purified by flash chromatography using (ethyl acetate:hexane, 1:9) to afford the title compound 21.25 g (Yield: 55.8%).

$^1$H-NMR (δ ppm): 1.47 (9H, s), 1.74-1.80 (2H, m), 1.91-1.96 (2H, m) 3.33-3.40 (2H, m), 3.66-3.72 (2H, m), 4.53-4.57 (1H, m), 6.94-6.96 (2H, d, J=8.78 Hz), 7.57-7.59 (2H, d, J=8.76 Hz);

Mass (m/z): 303.4 (M+H)$^+$.

Step (ii): Preparation of 4-(1-Cyclobutyl piperidin-4-yloxy)benzonitrile

To a stirred solution of 4-(4-Cyano phenoxy)piperidine-1-carboxylic acid tert-butyl ester (21.25 g, 0.0704 moles) in dichloromethane (300 mL) was added trifluoroacetic acid (81.4 g, 0.714 moles) and stirred the reaction mass overnight at room temperature. After completion of reaction, solvent was evaporated under vacuum and the residue, thus obtained, was basified with 10% caustic lye solution. The reaction mass was extracted with ethyl acetate twice, the combined organic layer was dried over sodium sulphate and evaporated under reduced pressure. The crude product, thus obtained, was treated with cyclobutanone (5.18 g, 0.074 moles), acetic acid (4.89 g, 0.0815 moles) in ethylene dichloride (100 mL), and stirred for 4 hours at room temperature. Sodium triacetoxyborohydride (35.06 g, 0.165 moles) was added to the reaction mass in a single lot and the mixture was stirred at room temperature for 2 hours. The reaction mixture was quenched in water and basified with lye solution. The layers were separated and the aqueous layer was extracted with dichloromethane twice. The combined organic layers were dried over sodium sulfate, concentrated under vacuum and the residual mass was further purified by flash chromatography (dichloromethane: triethylamine, 9.5:0.5) to obtain the title compound 10.92 g (Yield: 60.5%).

$^1$H-NMR (δ ppm): 1.67-1.76 (2H, m), 1.88-1.97 (2H, m), 2.04-2.14 (6H, m) 2.49 (2H, bs), 2.64-2.68 (2H, m), 2.85-2.91 (1H, m), 4.47-4.49 (1H, m), 6.92-6.94 (2H, d, J=8.8 Hz), 7.56-7.58 (2H, d, J=8.8 Hz);

Mass (m/z): 257.4 (M+H)$^+$.

Step (iii): Preparation of 4-(1-Cyclobutyl piperidin-4-yloxy)benzylamine

A solution of 4-(1-Cyclobutyl piperidin-4-yloxy)benzonitrile (8.22 g, 0.032 moles) in dry tetrahydrofuran (50 mL) was added to a stirred solution of lithium aluminium hydride (3.74 g, 0.098 moles) in dry tetrahydrofuran (30 mL), at 10 to 15° C. under nitrogen atmosphere. The resulting mass was further stirred for 20 minutes at ambient temperature and then refluxed for 4 hours. After completion of reaction, the mass was cooled to 10-15° C., quenched with water and basified with 4N sodium hydroxide solution. Reaction mass was filtered through celite and cake was washed with ethyl acetate. The separated organic layer was dried over sodium sulphate and concentrated under reduced pressure to obtain the title compound 7.17 g (Yield: 86.2%).

$^1$H-NMR (δ ppm): 1.65-1.72 (2H, m), 1.82-1.88 (4H, m), 1.96-2.05 (4H, m), 2.14 (2H, bs), 2.62 (2H, bs), 2.66-2.75 (1H, m), 3.79 (2H, m), 4.29-4.31 (1H, m), 6.85-6.88 (2H, d, J=8.5 Hz), 7.20-7.21 (2H, d, J=8.5 Hz);

Mass (m/z): 261.4 (M+H)$^+$.

Preparation 3: Preparation of tert-Butyl 4-[4-(2-chloro acetylamino)-3-fluoro phenoxy]piperidine-1-carboxylate Step (i): Preparation of tert-Butyl 4-(3-fluoro-4-nitro phenoxy)piperidine-1-carboxylate 3-Fluoro-4-nitro phenol (5 g, 0.032 moles), potassium carbonate (6.34 g, 0.047 moles) and tert-Butyl 4-(toluene-4-sulfonyloxy)piperidine-1-carboxylate (14 g, 0.04 moles) in dimethylformamide (50 mL) were stirred at 100° C. After completion of reaction, the mass was quenched on to water (100 mL) and extracted with ethyl acetate (2×100 mL). The resulting organic layer was washed with brine solution, dried over sodium sulfate and concentrated under reduced pressure to obtain the crude residue, which was further purified by flash chromatography using (ethyl acetate:hexane, 0.5:9.5) to afford the title compound 9.23 g (Yield: 85%).

$^1$H-NMR (δ ppm): 1.47 (9H, s), 1.75-1.82 (2H, m), 1.94-1.99 (2H, m), 3.35-3.41 (2H, m), 3.67-3.73 (2H, m), 4.54-4.59 (1H, m), 6.72-6.77 (2H, m), 8.07-8.11 (1H, m);

Mass (m/z): 341.3 (M+H)$^+$.

Step (ii): Preparation of tert-Butyl 4-(4-amino-3-fluoro phenoxy)piperidine-1-carboxylate tert-Butyl 4-(3-fluoro-4-nitro phenoxy)piperidine-1-carboxylate (9.22 g, 0.027 moles) was hydrogenated over 10% Pd/C (9.22 g) in methanol (92.2 mL) by bubbling hydrogen gas for 5 hours at ambient temperature. The mixture was filtered through a pad of celite, and the filtrate was concentrated under vacuum to obtain the title compound 7.54 g (Yield: 90%). The product was used as such in the next step without further purification.

$^1$H-NMR (δ ppm): 1.47 (9H, s), 1.75-1.82 (2H, m), 1.94-1.99 (2H, m), 3.35-3.41 (2H, m), 3.67-3.73 (2H, m), 4.54-4.59 (1H, m), 6.23-6.35 (3H, m);

Mass (m/z): 311.6 (M+H)$^+$.

Step (iii): Preparation of tert-Butyl 4-[4-(2-chloro acetylamino)-3-fluoro phenoxy]piperidine-1-carboxylate tert-Butyl 4-(4-amino-3-fluoro phenoxy)piperidine-1-carboxylate (7.54 g, 0.024 moles) was dissolved in dichloromethane (100 mL) and added triethylamine (3.6 g, 0.036 moles) at room temperature. To the resulting mass, a solution of chloro acetyl chloride (2.9 g, 0.026 moles) in dichloromethane (15 mL) was added drop wise at room temperature. After completion of the reaction, the organic mass was washed with water, dried over sodium sulfate, and concentrated under reduced pressure to obtain the crude residue, which was further purified by flash chromatography using (ethyl acetate:hexane, 1:5) to afford the title compound 5.94 g (Yield: 64%).

$^1$H-NMR (δ ppm: 1.47 (9H, s), 1.72-1.76 (2H, m), 1.89-1.94 (2H, m), 3.31-3.37 (2H, m), 3.65-3.71 (2H, m), 4.21 (2H, s), 4.40-4.44 (1H, m), 6.70-6.74 (2H, m), 8.03-8.07 (1H, t, J=8 Hz), 8.32 (1H, s);

Mass (m/z): 387.2 (M+H)$^+$, 389.1 (M+H)$^+$.

Example 1

Preparation of N-[4-(1-Cyclobutyl piperidin-4-yloxy)phenyl]-2-(morpholin-4-yl)-acetamide dihydrochloride Step (i): Preparation of 2-Chloro-N-[4-(1-cyclobutyl piperidin-4-yloxy)phenyl]acetamide Triethylamine (66.5 g, 0.658 moles) was added to a solution of 4-[(1-Cyclobutyl-4-piperidinyl)oxy]aniline (81 g, 0.329 moles, obtained in preparation 1) in dichloromethane (1 L), at 0° C. under nitrogen atmosphere. Then the resulting mass was treated with a solution of chloro acetyl chloride (44.6 g, 0.395 moles) in dichloromethane (1 L) drop wise at 0° C. and stirred at 0° C. for 1 hour. The reaction mixture was washed with water, dried over sodium sulfate and concentrated under vacuum and the crude compound thus obtained was purified by flash chromatography (methanol:chloroform, 2:8) to obtain the title compound 76.1 g (Yield: 72%).

$^1$H-NMR (δ ppm: 1.55-1.99 (12H, m), 2.49-2.67 (3H, m), 4.19 (2H, s), 4.26-4.28 (1H, m), 6.88-6.90 (2H, d, J=8.9 Hz), 7.44-7.46 (2H, d, J=8.9 Hz), 10.13 (1H, s);

Mass (m/z): 323.2 (M+H)$^+$.

Step (ii): Preparation of N-[4-(1-Cyclobutyl piperidin-4-yloxy)phenyl]-2-(morpholin-4-yl)acetamide A mixture of 2-Chloro-N-[4-(1-cyclobutyl piperidin-4-yloxy)phenyl]acetamide (76.0 g, 0.236, obtained in above step), morpholine (30.8 g, 0.353 moles) and potassium carbonate (98 g, 0.71 moles) in acetonitrile (1.5 L) was stirred for 5 hours at reflux temperature. The mixture was partitioned between ethyl acetate (1 L) and water (1 L). The layers were separated, and the aqueous layer was extracted with ethyl acetate (2×500 mL). The combined organic layers were washed with water twice, dried over sodium sulfate and concentrated under vacuum. The crude compound was purified by flash chromatography using (methanol:chloroform, 2:8) to afford the title compound 71 g (Yield: 80%).

$^1$H-NMR (δ ppm): 1.53-1.99 (12H, m), 2.46-2.68 (7H, m), 3.06 (2H, s), 3.60-3.63 (4H, m), 4.24-4.28 (1H, m), 6.85-6.88 (2H, d, J=8.9 Hz), 7.47-7.50 (2H, d, J=8.9 Hz), 9.5 (1H, s);

Mass (m/z): 374.2 (M+H)$^+$.

Step (iii): Preparation of N-[4-(1-Cyclobutyl piperidin-4-yloxy)phenyl]-2-(morpholin-4-yl) acetamide dihydrochloride To a stirred solution of N-[4-(1-Cyclobutyl piperidin-4-yloxy)phenyl]-2-(morpholin-4-yl)acetamide (70 g, 0.187 moles) in diethyl ether (2.3 L) and methanol (350 mL) was treated with 31.5% w/v methanolic hydrochloric acid (54.36 mL, 0.469 moles). The reaction mass was further stirred 2-3 hours at room temperature. The solvent was decanted and the resulting solid mass was washed with ether (3×250 mL) and dried under reduced pressure to obtain title compound 70 g (Yield: 83.9%).

IR (cm$^{-1}$): 2983, 2934, 2499, 1688, 1604, 1553, 1509, 1243, 1234, 1120, 830;

$^1$H-NMR (δ ppm): 1.63-1.75 (2H, m), 1.89-2.01 (2H, m), 2.11-2.15 (4H, m), 2.34-2.39 (2H, m), 2.80-2.90 (2H, m), 3.17-3.20 (2H, s), 3.21-3.26 (2H, m), 3.43-3.57 (2H, m), 3.69-3.73 (1H, m), 3.90-3.92 (2H, m), 4.15-4.16 (2H, m), 4.20-4.22 (2H, m), 4.48-4.50 (1H, m), 6.97-7.03 (2H, m), 7.51-7.54 (2H, m), 10.57 (1H, bs), 10.78 (1H, bs), 11.11 (1H, bs);

Mass (m/z): 374.2 (M+H)$^+$;

HPLC: 99.54%; M.P: 249.2-251.5° C.; Salt content: 16.09% (as dihydrochloride);

Example 2

Preparation of 2-[4-(1-Cyclobutyl piperidin-4-yloxy) phenylamino]-1-(morpholin-4-yl)ethanone hydrochloride Step (i): Preparation of 2-[4-(1-Cyclobutyl piperidin-4-yloxy)phenylamino]-1-(morpholin-4-yl)ethanone A mixture of 4-(1-Cyclobutyl piperidin-4-yloxy)aniline (0.5 g, 0.002 moles), 2-Chloro-1-(morpholin-4-yl)ethanone (0.5 g, 0.003) and potassium carbonate (0.56 g, 0.004 moles) in dimethylformamide (25 ml) was stirred at reflux temperature. After completion of reaction, the mixture was concentrated under reduced pressure and the residue was partitioned between ethyl acetate (250 mL) and water (250 mL). The combined organic layers were washed with brine solution, dried over sodium sulfate and concentrated under reduced pressure. The crude compound was purified by flash chromatography (chloroform: triethylamine, 9.5:0.5) to obtain the title compound 0.3 g (Yield: 40%).

Step (ii): Preparation of 2-[4-(1-Cyclobutyl piperidin-4-yloxy)phenylamino]-1-(morpholin-4-yl)ethanone hydrochloride To a stirred solution of 2-[4-(1-Cyclobutyl piperidin-4-yloxy)phenylamino]-1-(morpholin-4-yl)ethanone (0.3 g, 0.804 mmoles) in diethyl ether (20 mL) was treated with 15% methanolic hydrochloride (0.23 mL, 0.965 mmoles). The reaction mass was stirred further for 1 hour at room temperature. The solvent was decanted, the resulting solids were washed with ether (2×10 mL) and dried under reduced pressure to obtain title compound 0.28 g (Yield: 85%).

$^1$H-NMR (δ ppm): 1.65-1.75 (2H, m), 1.96-2.01 (2H, m), 2.08-2.17 (4H, m), 2.36-2.37 (2H, m), 2.80-2.90 (2H, m), 3.15-3.19 (1H, m), 3.34-3.48 (5H, m), 3.55-3.67 (4H, m), 4.22-4.26 (3H, m), 4.45-4.48 (1H, m), 4.64-4.68 (1H, m), 6.99-7.01 (2H, d, J=8 Hz), 7.19-7.21 (2H, m), 11.15 (1H, bs);

Mass (m/z): 374.4 (M+H)$^+$

Example 3

Preparation of N-[4-(1-Cyclobutyl piperidin-4-yloxy)-2-fluoro phenyl]-2-(morpholin-4-yl)acetamide dihydrochloride Step (i): Preparation of tert-Butyl 4-[3-fluoro-4-(2-(morpholin-4-yl)acetylamino) phenoxy]piperidine-1-carboxylate A mixture of tert-Butyl 4-[4-(2-Chloro acetylamino)-3-fluoro phenoxy]piperidine-1-carboxylate (3.31 g, 0.0085 moles, obtained in preparation 3), morpholine (0.89 g, 0.01 moles) and potassium carbonate (1.75 g, 0.012 moles) in acetonitrile (30 mL) was stirred for 5 hours at reflux temperature. The mixture was concentrated under reduced pressure and the residue, thus obtained, was partitioned between ethyl acetate (50 mL) and water (50 mL). The resulted aq. Phase was extracted with ethyl acetate (2×50 mL). The combined organic layers were washed with brine solution, dried over sodium sulfate and concentrated. The crude compound was purified by flash chromatography (ethyl acetate:hexane, 3:7) to obtain the title compound 3.1 g (Yield: 83.5%).

$^1$H-NMR (δ ppm): 1.47 (9H, s), 1.71-1.75 (2H, m), 1.89-1.92 (2H, m), 2.62-2.64 (4H, t, J=4 Hz), 3.16 (2H, s), 3.30-3.36 (2H, m), 3.65-3.71 (2H, m), 3.77-3.79 (4H, t, J=4 Hz), 4.39-4.42 (1H, m), 6.69-6.71 (2H, d, J=8 Hz), 8.11-8.18 (1H, t, J=8 Hz), 9.27 (1H, s);

Mass (m/z): 438.2 (M+H)$^+$.

Step (ii): Preparation of N-[4-(1-Cyclobutyl piperidin-4-yloxy)-2-fluoro phenyl]-2-(morpholin-4-yl) acetamide To a stirred solution of tert-Butyl 4-[3-fluoro-4-(2-(morpholin-4-yl)acetylamino) phenoxy]piperidine-1-carboxylate (3.1 g, 0.007 moles, obtained in above step) in dichloromethane (25 mL) was added trifluoroacetic acid (8.1 g, 0.071 moles) and stirred reaction mass overnight at room temperature. After completion of reaction, solvent was evaporated under vacuum and the residue, thus obtained, was basified with 10% caustic lye solution. Extracted the reaction mass with ethyl acetate twice, the combined organic layer dried over sodium sulphate and evaporated under reduced pressure. The crude product, thus obtained, was treated with cyclobutanone (0.6 g, 0.008 moles), in ethylene dichloride (30 mL), and stirred for 4 hours at room temperature. Sodium triacetoxyborohydride (3 g, 0.014 moles) was added to reaction mass in a single lot and the mixture was stirred at room temperature for 2 hours. The reaction mixture was quenched in water and basified with lye solution. The layers were separated and the aqueous layer was extracted with dichloromethane twice. The combined organic layers were dried over sodium sulfate, concentrated under vacuum and the residual mass was further purified by flash chromatography (dichloromethane: triethylamine, 9.5:0.5) to obtain the title compound 1.52 g (Yield: 55%).

$^1$H-NMR (δ ppm): 1.64-1.68 (3H, m), 1.70-1.73 (2H, m), 1.82-1.91 (4H, m), 1.96-2.05 (4H, m), 2.14-2.15 (2H, m), 2.62-2.64 (4H, m), 3.16 (2H, s), 3.77-3.79 (4H, t, J=4.0 Hz), 4.25-4.26 (1H, m), 6.68-6.70 (2H, m), 8.12-8.16 (1H, t, J=8.0 Hz), 9.20 (1H, bs);

Mass (m/z): 392.2 (M+H)$^+$.

Step (iii): Preparation of N-[4-(1-Cyclobutyl piperidin-4-yloxy)-2-fluoro phenyl]-2-(morpholin-4-yl) acetamide dihydrochloride Methanolic hydrochloride (2.08 ml, 0.009 moles, 15% w/v) was added to a stirred solution of N-[4-(1-Cyclobutyl piperidin-4-yloxy)-2-fluoro phenyl]-2-(morpholin-4-yl) acetamide (1.52 g, 0.004 moles) in diethyl ether (5 vol) and the reaction mass was further stirred for 2-3 hours at room temperature. The solvent was decanted; the resulting solids were washed with ether (2×10 mL) and dried under reduced pressure to obtain the title compound 1.6 g (Yield: 86.2%).

$^1$H-NMR (δ ppm): 1.63-1.72 (2H, m), 1.92-2.02 (2H, m), 2.13-2.21 (4H, m), 2.35-2.36 (3H, m), 2.80-2.89 (2H, m), 3.15-3.26 (4H, m), 3.56-3.70 (2H, m), 3.77-3.80 (2H, m), 3.90-3.91 (2H, m), 3.93-4.21 (2H, m), 4.55-4.76 (1H, m), 6.83-6.89 (1H, m), 7.04-7.07 (1H, m), 7.58-7.60 (1H, m), 10.39 (1H, bs), 10.55 (1H, bs), 11.05 (1H, bs);
Mass (m/z): 392.2 (M+H)+.

Example 4

Preparation of N-[4-(1-Cyclobutyl piperidin-4-yloxy)benzyl]morpholine-4-yl amide A solution of morpholine-4-carbonyl chloride (0.45 g, 0.003 moles), 4-(1-Cyclobutyl piperidin-4-yloxy)benzyl amine (0.5 g, 0.002 moles, obtain in preparation 2) and triethylamine (0.4 g, 0.004 moles) in dichloromethane (20 mL) was stirred at room temperature. After completion of reaction, the reaction mass was quenched on to water and extracted with dichloromethane. The combined organic layer was dried over sodium sulphate and concentrated under reduced pressure to obtain crude compound, which was further purified by flash chromatography (ethyl acetate: methanol, 98:2) to afford the title compound 0.45 g (Yield: 60%)
$^1$H-NMR (δ ppm): 1.66-1.78 (2H, m), 1.75-1.78 (2H, m), 2.07-2.19 (6H, m), 2.59 (2H, bs), 2.67-2.69 (2H, m), 2.93-2.97 (1H, m), 3.34-3.36 (4H, t, J=4.8), 3.67-3.69 (4H, t, J=4.5) 4.35-4.36 (2H, d, J=5.14), 4.41 (1H, bs) 4.66 (1H, bs), 6.84-6.86 (2H, d, J=8.4) 7.21-7.23 (2H, d, J=8.4);
Mass (m/z): 374.3 (M+H)+.

Examples 5-39

The compounds of Examples 5-39 were prepared by following the procedures as described in Examples 1 to 4, with some non-critical variations

| | | |
|---|---|---|
| 5. | N-[4-(1-Cyclobutyl piperidin-4-yloxy)-3-fluoro phenyl]-2-(morpholin-4-yl) acetamide | $^1$H-NMR (δ ppm): 1.42-1.87 (6H, m), 1.97-2.05 (8H, m), 2.61-2.63 (4H, t, J = 4.4 Hz), 2.78-2.8 (1H, m), 3.13 (2H, s), 3.76-3.79 (4H, t, J = 4.4 Hz), 4.02 (1H, m), 6.93-6.98 (1H, t, J = 8.8 Hz), 7.11-7.14 (1H, d, J = 8.6 Hz), 7.49-7.52 (1H, dd, J = 14.9, 2.4 Hz), 8.99 (1H, bs); Mass (m/z): 392 (M + H)+. |
| 6. | N-[4-(1-Cyclobutyl piperidin-4-yloxy)-2-methyl phenyl]-2-(3,3-difluoro pyrrolidin-1-yl) acetamide | $^1$H-NMR (δ ppm): 1.68-1.82 (6H, m), 2.01-2.05 (4H, m), 2.0-2.1 (2H, m), 2.22 (3H, s), 2.34-2.4 (2H, m), 2.5-2.61 (2H, m), 2.71-2.73 (1H, m), 2.97-3.01 (2H, t), 3.07-3.13 (2H, t, J = 4.0 Hz), 3.33 (2H, s), 4.28 (1H, m), 6.76-6.77 (2H, m), 7.77-7.79 (1H, m), 8.75 (1H, bs); Mass (m/z): 408 (M + H)+. |
| 7. | N-[4-(1-Cyclobutyl piperidin-4-yloxy)-2-trifluoromethyl phenyl]-2-(piperidin-1-yl) acetamide | $^1$H-NMR (δ ppm): 1.42-1.47 (2H, m), 1.62-1.67 (4H, m), 1.72-1.79 (2H, m), 1.78-1.8 (2H, m), 2.0-2.05 (6H, m), 2.25-2.35 (2H, m), 2.37-2.55 (4H, m), 2.6-2.64 (2H, m), 2.83-2.86 (1H, m), 3.08 (2H, s), 4.36-4.38 (1H, m), 7.05-7.08 (1H, dd, J = 9, 2.6 Hz), 7.13-7.14 (1H, d, J = 2.7 Hz), 8.22-8.24 (1H, d, J = 9 Hz), 9.85 (1H, bs); Mass (m/z): 440 (M + H)+. |
| 8. | N-[4-(1-Cyclopentyl piperidin-4-yloxy) phenyl]-2-(morpholin-4-yl) acetamide | $^1$H-NMR (δ ppm): 1.45-1.56 (4H, m), 1.69-1.71 (2H, m), 1.86-1.90 (4H, m), 2.03-2.08 (2H, m), 2.41-2.45 (2H, m), 2.61-2.63 (4H, t, J = 4.46 Hz), 2.80-2.83 (1H, m), 3.13 (2H, s), 3.58-3.61 (1H, m), 3.76-3.78 (4H, t, J = 4.5 Hz), 4.13-4.31 (1H, m), 6.87-6.9 (2H, d, J = 8.8 Hz), 7.44-7.46 (2H, d, J = 8.8 Hz), 8.93 (1H, bs); Mass (m/z): 388 (M + H)+. |
| 9. | N-[4-(1-Cyclobutyl piperidin-4-yloxy)-2-trifluoromethyl phenyl]-2-(morpholin-4-yl) acetamide | $^1$H-NMR (δ ppm): 1.68-1.73 (2H, m), 1.80-1.90 (4H, m), 1.97-2.06 (4H, m), 2.14-2.18 (2H, m), 2.63-2.65 (6H, m), 2.73-2.75 (1H, m), 3.15 (2H, s), 3.76-3.78 (4H, m), 4.32 (1H, m), 7.06-7.09 (1H, m), 7.14 (1H, d, J = 2.59 Hz), 8.19-8.21 (1H, d, J = 8.9 Hz), 9.65 (1H, bs); Mass (m/z): 442 (M + H)+. |
| 10. | N-[4-(1-Isopropyl-piperidin-4-yloxy)-2-methyl phenyl]-2-(pyrrolidin-1-yl) acetamide | $^1$H-NMR (δ ppm): 1.26-1.28 (6H, d), 1.84-1.87 (4H, m), 2.23 (3H, s), 2.70-2.73 (4H, m), 2.39 (2H, m), 2.87-2.89 (2H, m), 2.94-3.01 (5H, m), 3.49 (2H, s), 4.42-4.45 (1H, m), 6.47-6.77 (2H, m), 7.81-7.83 (1H, d, J = 9.2 Hz), 9.08 (1H, bs); Mass (m/z): 360.3 (M + H)+. |
| 11. | N-[4-(1-Cyclobutyl piperidin-4-yloxy)-2-methyl phenyl]-2-(pyrrolidin-1-yl) acetamide | $^1$H-NMR (δ ppm): 1.64-1.74 (5H, m), 1.85-1.86 (2H, m), 1.87-1.90 (3H, m), 2.06-2.22 (4H, m), 2.22-2.27 (5H, m), 2.60-2.62 (2H, m), 2.72-2.77 (5H, m), 3.31 (2H, s), 4.25-4.29 (1H, m), 6.75-6.77 (2H, m), 7.79-7.81 (1H, d, J = 8.0 Hz), 9.05 (1H, bs); Mass (m/z): 372 (M + H)+. |
| 12. | N-[4-(1-Cyclopentyl piperidin-4-yloxy)-2-methyl phenyl]-2-(piperidin-1-yl) acetamide | $^1$H-NMR (δ ppm): 0.86-0.9 (2H, m), 1.54-1.72 (8H, m), 1.85-1.87 (4H, m), 2.0-2.03 (3H, m), 2.23 (3H, s), 2.24-2.26 (2H, m), 2.35-2.65 (6H, m), 2.78-2.80 (2H, m), 3.10 (2H, s), 4.12-4.28 (1H, m), 6.76-6.78 (2H, m), 7.9-7.92 (1H, d, J = 8.8 Hz), 9.23 (1H, bs); Mass (m/z): 400 (M + H)+. |
| 13. | N-[4-(1-Cyclobutyl piperidin-4-yloxy)-2-methyl phenyl]-2-(piperidin-1-yl) acetamide | $^1$H-NMR (δ ppm): 0.86-0.9 (2H, m), 1.49-1.50 (2H, m), 1.61-2.01 (12H, m), 2.15-2.17 (2H, m), 2.25 (3H, s), 2.55-2.57 (6H, m), 2.67-2.77 (1H, m), 3.10 (2H, s), 4.10-4.28 (1H, m), 6.75-6.78 (2H, m), 7.89-7.91 (1H, d, J = 8.8 Hz), 9.23 (1H, bs); Mass (m/z): 386 (M + H)+. |
| 14. | N-[4-(1-Cyclobutyl piperidin-4-yloxy) phenyl]-N-methyl-2-(morpholin-4-yl) acetamide | $^1$H-NMR (δ ppm): 1.67-1.74 (3H, m), 2.02-2.05 (7H, m), 2.19-2.21 (2H, m), 2.38-2.4 (3H, m), 2.63-2.65 (2H, m), 2.75-2.84 (2H, m), 2.90 (2H, s), 3.22 (3H, s), 3.68-3.70 (4H, m), 4.30-4.34 (1H, m), 6.90-6.92 (2H, d, J = 8 Hz), 7.08-7.10 (2H, m); Mass (m/z): 388 (M + H)+. |
| 15. | N-[4-(1-Cyclopentyl piperidin-4-yloxy)-2-methyl phenyl]-2-(R-2-methyl pyrrolidin-1-yl) acetamide | $^1$H-NMR (δ ppm): 1.13-1.15 (3H, d, J = 6.0 Hz), 1.42-1.46 (2H, m), 1.54-1.57 (4H, m), 1.69-1.69 (2H, m), 1.78-1.86 (6H, m), 1.97-2.02 (2H, m), 2.22 (3H, s), 2.31-2.34 (2H, m), 2.39-2.44 (1H, m), 2.52-2.67 (2H, m), 2.7-2.79 (2H, m), 3.06-3.1 (1H, d, J = 16.9 Hz), 3.21-3.25 (1H, m), 3.45-3.49 (1H, d, J = 16.9 Hz), 4.23-4.27 (1H, m), 6.76-6.88 (2H, d, J = 8.5 Hz), 7.84-6.86 (1H, d, J = 8.5 Hz), 9.21 (1H, bs); Mass (m/z): 400 (M + H)+. |

| | | |
|---|---|---|
| 16. N-[4-(1-Cyclobutyl piperidin-4-yloxy)-2-methyl phenyl]-2-(R-2-methyl pyrrolidin-1-yl) acetamide | $^1$H-NMR (δ ppm): 1.13-1.14 (4H, d, J = 6.0 Hz), 1.67-1.82 (6H, m), 1.89-2.06 (10H, m), 2.1-2.15 (2H, m), 2.22 (3H, s), 2.43-2.63 (2H, m), 3.06-3.1 (1H, d, J = 16.9 Hz), 3.20-3.23 (1H, m), 3.44-3.49 (1H, d, J = 16.9 Hz), 4.22-4.27 (1H, m), 6.75-6.78 (2H, m), 7.83-6.86 (1H, d, J = 8.7 Hz), 9.21 (1H, bs); Mass (m/z): 386 (M + H)$^+$. | |
| 17. N-[4-(1-Cyclobutyl piperidin-4-yloxy)-2-methoxy phenyl]-2-(morpholin-4-yl) acetamide | $^1$H-NMR (δ ppm): 1.65-1.78 (2H, m), 1.91-1.94 (2H, m), 2.08-2.17 (6H, m), 2.51-2.54 (2H, m), 2.62-2.64 (4H, t), 2.70-2.72 (2H, m), 2.92-2.96 (1H, m), 3.14 (2H, s), 3.77-3.85 (4H, t), 3.88 (3H, s), 4.3-4.39 (1H, m), 6.46-6.49 (2H, m), 8.20-8.22 (1H, d, J = 9.2 Hz), 9.54 (1H, bs); Mass (m/z): 404 (M + H)$^+$. | |
| 18. N-[4-(1-Cyclobutyl piperidin-4-yloxy)-2-trifluoromethyl phenyl]-2-(4-hydroxy piperidin-1-yl) acetamide | $^1$H-NMR (δ ppm): 1.6-1.73 (9H, m), 2.02-2.06 (6H, m), 2.17-2.19 (2H, m), 2.42-2.46 (2H, m), 2.58-2.61 (2H, m), 2.74-2.77 (1H, m), 2.84-2.87 (2H, m), 3.14 (2H, s), 3.79 (1H, m), 4.30-4.33 (1H, m), 7.06-7.09 (1H, dd, J = 12.0, 2.4 Hz), 7.14-7.15 (1H, d, J = 2.8 Hz), 8.22-8.23 (1H, d, J = 12 Hz), 9.74 (1H, bs); Mass (m/z): 456 (M + H)$^+$. | |
| 19. N-[4-(1-Cyclobutyl piperidin-4-yloxy) phenyl]-2-(4-hydroxy piperidin-1-yl) acetamide | $^1$H-NMR (δ ppm): 1.66-1.76 (4H, m), 1.87-1.97 (4H, m), 2.03-2.05 (6H, m), 2.38-2.43 (4H, m), 2.64-2.65 (2H, m), 2.86-2.95 (4H, m), 3.11 (2H, s), 3.77-3.80 (1H, m), 4.30-4.33 (1H, m), 6.86-6.89 (2H, dd), 7.44-7.46 (2H, dd), 9.04 (1H, bs); Mass (m/z): 388 (M + H)$^+$ | |
| 20. N-[4-(1-Cyclopentyl piperidin-4-yloxy)-2-fluoro phenyl]-2-(morpholin-4-yl) acetamide dihydrochloride | $^1$H-NMR (δ ppm): 1.53-1.55 (2H, m), 1.73-1.79 (4H, m), 2.01-2.04 (5H, m), 2.09-2.21 (2H, m), 3.04-3.07 (2H, m), 3.20-3.37 (4H, m), 3.52-3.55 (2H, m), 3.80-3.97 (4H, m), 4.23 (2H, m), 4.58-4.60 (1H, m), 6.85-6.94 (1H, m), 7.05-7.11 (1H, m), 7.59-7.63 (1H, m), 10.4 (1H, bs), 10.5 (1H, bs), 10.67 (1H, m); Mass (m/z): 406.2 (M + H)$^+$. | |
| 21. N-[4-(1-Cyclobutyl piperidin-4-yloxy)-phenyl]-2-(pyrrolidin-1-yl) acetamide | $^1$H-NMR (δ ppm): 1.65-1.72 (4H, m), 1.72-1.87 (8H, m), 2.03-2.14 (2H, m), 2.62-2.65 (2H, m), 2.69-2.75 (7H, m), 3.26 (2H, s), 4.25-4.27 (1H, m), 6.87-6.89 (2H, dd), 7.45-7.47 (2H, dd), 8.97 (1H, bs); Mass (m/z): 358 (M + H)$^+$. | |
| 22. N-[4-(1-Isopropyl piperidin-4-yloxy)-phenyl]-2-(morpholin-4-yl) acetamide | $^1$H-NMR (δ ppm): 1.06-1.08 (6H, d, J = 6.48 Hz), 1.63 (2H, m), 1.80-1.84 (2H, m), 2.01-2.02 (2H, m), 2.40 (2H, m), 2.61-2.64 (4H, t, J = 4.5 Hz), 3.13 (2H, s), 4.35 (1H, m), 3.77-3.79 (4H, t, J = 4.5 Hz), 4.26-4.27 (1H, m), 6.88-6.90 (2H, d, J = 8.8 Hz), 7.44-7.46 (2H, d, J = 8.8 Hz), 8.92 (1H, bs); Mass (m/z): 362.3 (M + H)$^+$. | |
| 23. N-[4-(1-Cyclopropyl piperidin-4-yloxy) phenyl]-2-(morpholin-4-yl) acetamide | $^1$H-NMR (δ ppm): 0.76-0.78 (2H, m), 1.13 (2H, m), 1.93-1.99 (2H, m), 2.16-2.19 (2H, m), 3.33-3.39 (6H, m), 3.42-3.44 (3H, m), 3.76-3.77 (2H, m), 3.80-3.83 (2H, m), 4.18 (2H, m), 4.51 (1H, m), 6.97-6.05 (2H, dd), 7.52-7.56 (2H, dd), 8.92 (1H, bs); Mass (m/z): 360.3 (M + H)$^+$. | |
| 24. N-[4-(1-Cyclobutyl piperidin-4-yloxy) phenyl]-2-(4-isopropyl[1,4]diazepan-1-yl) acetamide | $^1$H-NMR (δ ppm): 1.17-1.19 (6H, d, J = 6.54 Hz), 1.61-1.63 (3H, m), 1.90-1.98 (8H, m), 2.30-2.35 (2H, m), 2.49-2.55 (2H, m), 2.70-2.72 (2H, m), 2.91-2.94 (2H, m), 3.01-3.07 (4H, m), 3.15-3.19 (5H, m), 4.30-4.33 (1H, m), 6.88-6.99 (2H, dd, J = 8.9 Hz), 7.49-7.51 (2H, dd, J = 8.8 Hz), 8.95 (1H, bs); Mass (m/z): 429.1 (M + H)$^+$. | |
| 25. N-[4-(1-Cyclobutyl piperidin-4-yloxy) phenyl]-2-(2-hydroxymethyl morpholin-4-yl) acetamide | $^1$H-NMR (δ ppm): 1.68-1.72 (3H, m), 1.89-1.97 (3H, m), 2.13-2.19 (5H, m), 2.33-2.36 (2H, m), 2.80-2.86 (3H, m), 3.07-3.10 (1H, m), 3.17-3.20 (3H, m), 3.69-3.72 (1H, m), 3.82-3.85 (2H, m), 3.99-4.01 (1H, m), 4.03 (1H, m), 4.48-4.51 (1H, m), 4.70 (1H, m), 6.97-7.03 (2H, dd), 7.51-7.54 (2H, dd), 8.83 (1H, bs); Mass (m/z): 404.5 (M + H)$^+$. | |
| 26. N-[4-(1-Cyclobutyl piperidin-4-yloxy) phenyl]-3-(morpholin-4-yl) propionamide | $^1$H-NMR (δ ppm): 1.63-1.68 (3H, m), 1.83-1.87 (1H, m), 1.97-2.02 (3H, m), 2.13-2.16 (3H, m), 2.30-2.35 (3H, m), 2.78-2.89 (4H, m), 3.06-3.09 (3H, m), 3.17-3.20 (2H, m), 3.58-3.61 (3H, m), 3.94-3.97 (2H, m), 4.67 (1H, m), 6.92-6.99 (2H, dd, J = 8.8 Hz), 7.49-7.51 (2H, dd, J = 8.8 Hz), 8.85 (1H, bs); Mass (m/z): 388.2 (M + H)$^+$. | |
| 27. N-[4-(1-Cyclopentyl piperidin-4-yloxy) phenyl]-2-(piperidin-1-yl) acetamide dihydrochloride | $^1$H-NMR (δ ppm): 1.17-1.23 (2H, m), 1.31-1.32 (2H, m), 1.71-1.72 (9H, m), 1.74-1.77 (4H, m), 1.98-2.01 (2H, m), 3.01-3.06 (4H, m), 3.38-3.40 (4H, m), 4.06-4.07 (2H, m), 4.50-4.52 (1H, m), 6.97-7.03 (2H, m), 7.50-7.54 (2H, m), 9.7 (1H, bs), 10.48 (1H, bs), 10.48 (1H, bs); Mass (m/z): 386.5 (M + H)$^+$. | |
| 28. N-[4-(1-Cyclopentyl piperidin-4-yloxy) phenyl]-2-(pyrrolidin-1-yl) acetamide dihydrochloride | $^1$H-NMR (δ ppm): 1.52-1.60 (3H, m), 1.71-1.75 (2H, m), 1.80-1.81 (3H, m), 1.98-2.00 (8H, m), 2.97-3.11 (6H, m), 3.58-3.60 (3H, m), 4.21 (2H, s), 4.49-4.54 (1H, m), 6.96-7.03 (2H, dd, J = 8.0 Hz), 7.52-7.52 (2H, dd, J = 8 Hz), 8.86 (1H, bs), 10.31 (1H, bs), 10.77 (1H, bs), 10.99 (1H, bs); Mass (m/z): 372.1 (M + H)$^+$. | |

| | | |
|---|---|---|
| 29. N-[4-(1-Cyclobutyl piperidin-4-yloxy) phenyl]-2-(piperidin-1-yl) acetamide | $^1$H-NMR (δ ppm): 1.68-1.73 (2H, m), 1.77-1.90 (4H, m), 2.01-2.13 (2H, m), 2.15-2.19 (4H, m), 2.33-2.37 (2H, m), 2.83-2.90 (2H, m), 3.01-3.03 (2H, m), 3.04-3.06 (2H, m), 3.17-3.20 (2H, m), 3.34-3.39 (2H, m), 3.57-3.70 (1H, m), 4.07 (2H, s), 4.48-4.50 (1H, m), 6.97-7.03 (2H, dd, J = 12.0 Hz), 7.51-7.54 (2H, dd, J = 12.0 Hz), 8.93 (1H, bs); Mass (m/z): 372.4 (M + H)$^+$. | |
| 30. N-[4-(1-Cyclobutyl piperidin-4-yloxy)-2-trifluoromethyl phenyl]-2-(pyrrolidin-1-yl) acetamide dihydrochloride | $^1$H-NMR (δ ppm): 1.68-1.73 (3H, m), 1.88-1.90 (3H, m), 2.02-2.03 (5H, m), 2.39-2.40 (2H, m), 2.91-2.99 (2H, m), 3.06-3.10 (2H, m), 3.15-3.38 (2H, m), 3.55-3.58 (2H, m), 3.74-3.85 (2H, m), 4.23 (2H, s), 4.70-4.71 (1H, m), 7.31-7.33 (1H, d, J = 8.0 Hz), 7.36-7.42 (2H, m), 9.51 (1H, bs), 10.29 (1H, bs), 10.36 (1H, bs), 11.35 (1H, bs); Mass (m/z): 426.1 (M + H)$^+$. | |
| 31. N-[4-(1-Cyclobutyl piperidin-4-yloxy) phenyl]-N-(2-morpholin-4-yl ethyl) acetamide | $^1$H-NMR (δ ppm): 1.66-1.75 (7H, m), 1.87-1.88 (2H, m), 2.05-2.09 (6H, m), 2.43-2.48 (7H, m), 2.67 (2H, bs), 3.65-3.67 (4H, t, J = 4.4 Hz), 3.78-3.81 (2H, t), 4.4 (1H, m), 6.89-6.91 (2H, d, J = 8.7 Hz), 7.10-7.13 (2H, d, J = 8.7 Hz); Mass (m/z): 402.4 (M + H)$^+$. | |
| 32. [4-(1-Cyclobutyl piperidin-4-yloxy) phenyl]-(2-morpholin-4-yl ethyl) amine | $^1$H-NMR (δ ppm): 1.64-1.72 (2H, m), 1.77-1.93 (6H, m), 2.02-2.05 (2H, m), 2.07-2.08 (2H, m), 2.47-2.5 (4H, m), 2.61-2.63 (4H, m), 2.70-2.74 (1H, m), 3.11-3.13 (2H, t), 3.71-3.73 (4H, t), 4.10 (1H, m), 6.57-6.60 (2H, d, J = 8.7 Hz), 6.79-6.82 (2H, d, J = 8.7 Hz); Mass (m/z): 360.4 (M + H)$^+$. | |
| 33. N-[4-(1-Cyclobutyl piperidin-4-yloxy) phenyl]-2-(R-2-hydroxymethyl pyrrolidin-1-yl) acetamide L (+) tartarate | $^1$H-NMR (δ ppm): 1.81-1.91 (5H, m), 2.05-2.16 (5H, m), 2.30-2.35 (4H, m), 2.72-2.74 (1H, m), 3.05-3.17 (4H, m), 3.31-3.35 (2H, m), 3.43-3.47 (1H, m), 3.62-3.71 (3H, m), 3.83-3.87 (1H, m), 4.40 (2H, s), 4.63-4.66 (1H, m), 6.97-6.99 (2H, dd, J = 8.2, 2.04 Hz), 7.51-7.53 (2H, dd, J = 8.2, 2.00 Hz); Mass (m/z): 388.3 (M + H)$^+$. | |
| 34. N-[2-(1-Cyclobutyl piperidin-4-yloxy) pyridin-5-yl]-N-[2-(morpholin-4-yl) ethyl] acetamide | $^1$H-NMR (δ ppm): 1.66-1.73 (6H, m), 1.89 (2H, m), 1.97-2.18 (6H, m), 2.42-2.48 (6H, m), 2.76 (2H, bs), 2.98-3.03 (2H, m), 3.60-3.66 (4H, m), 3.77-3.80 (2H, t), 4.55 (1H, m), 6.74-6.76 (1H, d, J = 8.6 Hz), 7.46-7.48 (1H, dd, J = 8.6, 2.6 Hz), 8.01-8.02 (1H, d, J = 2.4 Hz); Mass (m/z): 403.3 (M + H)$^+$. | |
| 35. N-[2-(1-Cyclobutyl piperidin-4-yloxy) pyridin-5-yl]-2-(piperidin-1-yl) acetamide | $^1$H-NMR (δ ppm): 1.63-1.66 (8H, m), 1.81-1.83 (3H, m), 2.03-2.06 (6H, m), 2.18-2.13 (4H, m), 2.54-2.55 (4H, m), 3.08 (2H, s), 5.03 (1H, m), 6.70-6.72 (1H, d, J = 8.8 Hz), 7.92-7.95 (1H, dd, J = 8.8, 2.6 Hz), 8.18-8.19 (1H, d, J = 2.6 Hz), 9.15 (1H, bs); Mass (m/z): 373.3 (M + H)$^+$. | |
| 36. N-[2-(1-Cyclobutyl piperidin-4-yloxy) pyridin-5-yl]-2-(morpholin-4-yl) acetamide | $^1$H-NMR (δ ppm): 1.51-1.95 (12H, m), 2.43-2.65 (7H, m), 3.06 (2H, s), 3.60-3.79 (4H, m), 5.22 (1H, m), 6.70-6.73 (1H, d, J = 8.8 Hz), 7.98-8.00 (1H, dd, J = 8.5 Hz, 2.4 Hz), 8.16-8.18 (1H, d, J = 2.4 Hz), 8.97 (1H, bs); Mass (m/z): 375.4 (M + H)$^+$. | |
| 37. N-[4-(1-Cyclobutyl piperidin-4-yloxy)-2-fluoro phenyl]-N-[2-(morpholin-4-yl)-ethyl] acetamide | $^1$H-NMR (δ ppm): 1.63-1.76 (7H, m), 1.85-1.89 (2H, m), 2.05-2.09 (6H, m), 2.43-2.48 (7H, m), 2.67 (2H, bs), 3.65-3.67 (4H, t, J = 4.4 Hz), 3.78-3.81 (2H, t), 4.4 (1H, m), 6.89-6.91 (2H, m), 7.10-7.8 (1H, m); Mass (m/z): 420.4 (M + H)$^+$. | |
| 38. N-[4-(1-Cyclopropyl piperidin-4-yloxy) phenyl]-N-[2-(morpholin-4-yl) ethyl] acetamide L(+) tartarate | $^1$H-NMR (δ ppm): 0.81-0.85 (4H, m), 1.83 (3H, s), 1.90-2.02 (2H, m), 2.10-2.2 (2H, m), 2.40-2.50 (1H, m), 2.66-2.69 (6H, m), 3.18-3.22 (2H, m), 3.36-3.39 (2H, m), 3.70-3.73 (4H, m), 3.86-3.90 (2H, m), 4.60-4.70 (1H, m) 7.07-7.09 (2H, d, J = 8.7 Hz), 7.26-7.28 (2H, d, J = 8.7 Hz); Mass (m/z): 388.4 (M + H)$^+$. | |
| 39. N-[4-(1-Cyclobutyl piperidin-4-yloxy) phenyl]-2-(1-acetyl piperazin-4-yl) acetamide | $^1$H-NMR (δ ppm): 1.69-1.74 (3H, m), 1.76-1.80 (3H, m), 2.01-2.10 (4H, m), 2.12 (3H, s), 2.59-2.64 (8H, m), 2.75-2.80 (1H, m), 3.17 (2H, s), 3.53-3.56 (2H, m), 3.6-3.65 (2H, m), 4.3-4.4 (1H, m), 6.88-6.9 (2H, d, J = 8.88 Hz), 7.44-7.46 (2H, d, J = 8.84 Hz), 8.8 (1H, bs); Mass (m/z): 415.2 (M + H)$^+$. | |

Examples-40-51

The person skilled in the art can prepare the compounds of Examples-40-51 by following the procedures described above.

40. N-[4-(1-Cyclobutyl piperidine-4-yloxy)-2-methyl phenyl]-2-(4-hydroxy piperidin-1-yl) acetamide
41. N-[4-(1-Cyclopropyl piperidin-4-yloxy) phenyl]-2-(R-2-hydroxymethyl pyrrolidin-1-yl) acetamide
42. N-[4-(1-Cyclobutyl piperidin-4-yloxy) benzyl]-2-(morpholin-4-yl) acetamide
43. N-[4-(1-Cyclobutyl piperidin-4-yloxy)-2-fluoro benzyl]-2-(morpholin-4-yl) acetamide
44. N-[4-(1-Cyclobutyl piperidin-4-yloxy) phenyl]-2-(3-hydroxy azetidin-1-yl) acetamide
45. N-[4-(1-Cyclobutyl piperidin-4-yloxy)-2-fluoro phenyl]-2-(3-methoxy azetidin-1-yl) acetamide
46. N-[4-(1-Cyclobutyl piperidin-4-yloxy)-2-fluoro phenyl]-2-(2-hydroxymethyl pyrrolidin-1-yl) acetamide 47. N-[2-Chloro-4-(1-cyclobutyl piperidin-4-yloxy) phenyl]-2-(morpholin-4-yl) acetamide
48. N-[2-Chloro-4-(1-cyclobutyl piperidin-4-yloxy) phenyl]-2-(piperidin-1-yl) acetamide
49. N-[4-(1-Cyclobutyl piperidin-4-yloxy) phenyl]-2-(tetrahydro pyran-4-yloxy) acetamide
50. 2-[4-(1-Cyclobutyl piperidin-4-yloxy)-2-fluoro phenylamino]-1-(morpholin-4-yl) ethanone
51. N-[4-(1-Cyclobutyl piperidin-4-yloxy)-2-fluoro phenyl]-N-(2-morpholin-4-yl ethyl) acetamide Biological Assays

Example 52

Binding and Functional Assays for Human or Rat Histamine H3 Receptor

Compounds can be evaluated according to the following procedures.

Materials and Methods:
  Receptor source: Rat brain frontal cortex or recombinant human cDNA expressed in CHO cells
  Radioligand: [$^3$H] R-α-methylhistamine
  Final ligand concentration—[3.0 nM]
  Non-specific determinant: R-α-methylhistamine (100 uM)
  Reference compound: R-α-methylhistamine
  Positive control: R-α-methylhistamine Incubation conditions:
  Increasing concentrations of test compounds or standard were incubated with membrane receptors and radioligand in 5 mM $MgCl_2$ and 50 mM TRIS-HCl (pH 7.4) for 60 minutes at room temperature. The reaction was terminated by rapid vacuum filtration onto the glass fiber filters. Radioactivity trapped onto the filters was determined and compared to the control values in order to ascertain any interactions of the test compound(s) with either cloned human or rat receptor binding site.

| Example Number | $K_i$ (nM) |
|---|---|
| 1. | 8.7 |
| 2. | 6.4 |
| 3. | 14.9 |
| 7. | 14.8 |
| 10. | 8.4 |
| 11. | 1.9 |
| 12. | 7.5 |
| 13. | 3.3 |
| 14. | 4.9 |
| 15. | 4 |
| 16. | 2.4 |
| 19. | 6.4 |
| 21. | 1.1 |
| 22. | 8.3 |
| 24. | 1.0 |
| 25. | 4.05 |
| 26. | 6.7 |
| 27. | 4.1 |
| 28. | 3.8 |
| 29. | 1.6 |
| 37. | 9.73 |
| 38. | 6.6 |
| 39. | 5.39 |

Literature Reference: Millipore Data Sheet

Example 53

Rodent Pharmacokinetic Study

Male Wistar rats (230-280 grams) obtained from NIN (National Institute of Nutrition, Hyderabad, India) were used as an experimental animal. Three animals were housed in each cage. Animals were kept fasted over night and maintained on a 12 hours light/dark cycle. Three rats were dosed New chemical entity (NCE) orally (3 or 10 mg/kg) and intravenously (1 or 5 mg/kg) on day 0 and day 2.

At each time point blood was collected by jugular vein. Blood was stored at 2-8° C. until analysis. The concentrations of the NCE compound in blood were determined using LC-MS/MS method. Schedule time points: Pre dose 0.08, 0.25, 0.5, 1, 2, 4, 6, 8 and 24 hours after dosing (n=3). The NCE compounds were quantified in blood by partially validated LC-MS/MS method using acetonitrile precipitation technique. NCE compounds were quantified in the calibration range of 1-2000 ng/mL in blood. Study samples were analyzed using calibration samples in the batch and quality control samples spread across the batch.

Pharmacokinetic parameters were calculated by non-compartmental model using software WinNonlin version 5.0.1.

| Example Number | Strain/Gender | Dose (mg/kg) | Vehicle | Route of administration | $C_{max}$ (ng/mL) | $T_{max}$ (h) | $AUC_t$ (ng · hr/mL) | $T_{1/2}$ (h) | Bioavailability (%) |
|---|---|---|---|---|---|---|---|---|---|
| 1. | Wistar/Male | 1 | Water | Intravenous | | | 263 ± 21 | 1.45 ± 0.24 | 79 ± 11 |
| | | 3 | Water | Per Oral | 349 ± 35 | 0.42 ± 0.14 | 626 ± 118 | 1.53 ± 0.41 | |
| 3. | Wistar/Male | 1 | Water | Intravenous | | | 173 ± 60 | 0.56 ± 0.19 | 35 ± 5 |
| | | 3 | Water | Per Oral | 129 ± 34 | 0.42 ± 0.14 | 174 ± 43 | 1.46 ± 0.75 | |
| 11. | Wistar/Male | 5 | Water | Intravenous | | | 3345 ± 656 | 26.31 ± 5.17 | 20 ± 9 |
| | | 10 | Water | Per Oral | 122 ± 55 | 4.0 ± 1.76 | 1349 ± 569 | 10.75 ± 1.92 | |
| 19. | Wistar/Male | 1 | Water | Intravenous | | | 347 ± 44 | 17.00 ± 4.50 | 81 ± 12 |
| | | 3 | Water | Per Oral | 67 ± 11 | 2.67 ± 1.15 | 838 ± 96 | 12.83 ± 2.48 | |
| 22. | Wistar/Male | 1 | Water | Intravenous | | | 340 ± 60 | 2.04 ± 0.45 | 85 ± 12 |
| | | 3 | Water | Per Oral | 376 ± 27 | 0.42 ± 0.14 | 850 ± 61 | 2.47 ± 0.26 | |
| 23. | Wistar/Male | 1 | Water | Intravenous | | | 338 ± 29 | 1.13 ± 0.02 | 55 ± 10 |
| | | 3 | Water | Per Oral | 389 ± 29 | 0.50 ± 0.00 | 556 ± 111 | 1.23 ± 0.53 | |
| 37. | Wistar/Male | 1 | Water | Intravenous | | | 68 ± 2 | 3.30 ± 0.42 | 32 ± 8 |
| | | 3 | Water | Oral | 27 ± 11 | 0.50 ± 0.00 | 64 ± 16 | 3.59 ± 0.43 | |

Example 54

Rodent Brain Penetration Study

Male Wister rats (230-280 grams) obtained from NIN (National Institute of Nutrition, Hyderabad, India) was used as experimental animals. Three animals were housed in each cage. Animals were given water and food ad libitum throughout the experiment, and maintained on a 12 hours light/dark cycle.

New chemical entity (NCE) was dissolved in suitable vehicle and administered orally (3 or 10 mg/kg). Around $T_{max}$ (i.e, 0.5 hour, 1.0 hour and 2.0 hours) animals were sacrificed. Blood and brain tissue were collected and brain was homogenized to yield 20% w/v. Blood was stored at 2-8° C. and brain homogenate was frozen at −20° C. until analysis. The concentrations of NCE in blood and brain were quantified using LC-MS/MS method.

The NCE was quantified in blood and brain homogenate by partially validated LC-MS/MS method using acetonitrile precipitation technique. NCE compounds were quantified in the calibration range of 1-500 ng/mL in blood and brain homogenate. Study samples were analyzed using calibration samples in the batch and quality control samples spread across the batch. Extents of brain-blood ratio were calculated ($C_{brain}/C_{blood}$)

| Example Number | Strain/ Gender | Dose (mg/kg) | Vehicle | Route of administration | Brain Penetration Ratio ($C_{brain}/C_{blood}$) |
|---|---|---|---|---|---|
| 1. | Wistar/ Male | 3 | Water | Per Oral | 0.93 ± 0.05 |
| 3. | Wistar/ Male | 3 | Water | Per Oral | 2.07 ± 0.07 |
| 37. | Wistar/ Male | 3 | Water | Per Oral | 1.24 ± 0.18 |

Example 55

Object Recognition Task Model

The cognition enhancing properties of compounds of this invention were estimated by using this model.

Male Wister rats (230-280 grams) obtained from N. I. N. (National Institute of Nutrition, Hyderabad, India) was used as experimental animals. Four animals were housed in each cage. Animals were kept on 20% food deprivation before one day and given water ad libitum throughout the experiment and maintained on a 12 hours light/dark cycle. Also the rats were habituated to individual arenas for 1 hour in the absence of any objects.

One group of 12 rats received vehicle (1 mL/Kg) orally and another set of animals received compound of the formula (I) either orally or i.p., before one hour of the familiar (T1) and choice trial (T2).

The experiment was carried out in a 50×50×50 cm open field made up of acrylic. In the familiarization phase, (T1), the rats were placed individually in the open field for 3 minutes, in which two identical objects (plastic bottles, 12.5 cm height×5.5 cm diameter) covered in yellow masking tape alone (a1 and a2) were positioned in two adjacent corners, 10 cms from the walls. After 24 hours of the (T1) trial for long-term memory test, the same rats were placed in the same arena as they were placed in T1 trial. Choice phase (T2) rats were allowed to explore the open field for 3 minutes in presence of one familiar object (a3) and one novel object (b) (Amber color glass bottle, 12 cm high and 5 cm in diameter). Familiar objects presented similar textures, colors and sizes. During the T1 and T2 trial, explorations of each object (defined as sniffing, licking, chewing or having moving vibrissae whilst directing the nose towards the object at a distance of less than 1 cm) were recorded separately by stopwatch. Sitting on an object was not regarded as exploratory activity, however, it was rarely observed.

T1 is the total time spent exploring the familiar objects (a1+a2).

T2 is the total time spent exploring the familiar object and novel object (a3+b).

The object recognition test was performed as described by Ennaceur, A., Delacour, J., 1988, A new one-trial test for neurobiological studies of memory in rats—Behavioural data, Behav. Brain Res., 31, 47-59.

| Example Number | Dose mg/kg, p.o. | Exploration time mean ± S.E.M (sec) | | Inference |
|---|---|---|---|---|
| | | Familiar object | Novel object | |
| 1. | 0.3 mg/kg | 5.56 ± 0.81 | 15.36 ± 1.74 | Active |
| 3. | 3 mg/kg | 6.77 ± 0.44 | 12.49 ± 1.59 | Active |
| 22. | 1 mg/kg | 7.12 ± 1.51 | 16.50 ± 2.37 | Active |
| 37. | 3 mg/kg | 5.53 ± 1.67 | 14.18 ± 2.04 | Active |

Example 56

Morris Water Maze

The cognition enhancing properties of compounds of this invention were estimated by using this model.

The water maze apparatus consisted of a circular pool (1.8 m diameter, 0.6 m high) constructed in black Perspex (TSE systems, Germany) filled with water (24±2° C.) and positioned underneath a wide-angled video camera to track animal. The 10 cm² perspex platform, lying 1 cm below the water surface, was placed in the centre of one of the four imaginary quadrants, which remained constant for all rats. The black Perspex used in the construction of the maze and platform offered no intramaze cues to guide escape behavior. By contrast, the training room offered several strong extramaze visual cues to aid the formation of the spatial map necessary for escape learning. An automated tracking system, [Videomot 2 (5.51), TSE systems, Germany] was employed. This program analyzes video images acquired via a digital camera and an image acquisition boards that determined path length, swim speed and the number of entries and duration of swim time spent in each quadrant of the water maze.

| Example Number | Reversal of Scopolamine Induced amnesia |
|---|---|
| 1. | ≤1 mg/kg, p.o. |

Example 57

Inhibition of Food Intake

The anti-obesity properties of compounds of this invention were estimated using this model.

The experiment consisted of 6 days. The rats were adapted to the 18 hours fasting and 6 hours feeding pattern. The animals were housed in a group of three in the cages provided with the fasting grills and was fasted for 18 hours. After 18 hours fasting the rats were separated and placed individually in the cage. Weighed amount of feed was provided to rats for 6 hours and the feed intake at 1 hour, 2 hours, 4 hours and 6 hours was measured.

Again the rats were regrouped and fasted for 18 hours. The above procedure was followed for 5 days. The average cumulative food intake by the rats on the last 3 days was calculated. Animals were randomized on the basis of their previous three days food intake. On the day of experiment the rats were orally treated test compounds or vehicle. After 60 minutes, the feed was provided to the rats and the food intake at 1 hour, 2 hours, 4 hours and 6 hours was measured. The food intake by the rats treated with test compound was compared with the vehicle treated group by using Unpaired Student's t test.

| Example Number | Inhibition of food intake |
|---|---|
| 13. | 30 mg/kg, p.o. |
| 16. | ≥30 mg/kg, p.o. |
| 21. | ≥30 mg/kg, p.o. |
| 22. | 60 mg/kg, p.o. |

We claim:
1. A compound of the general formula (I):

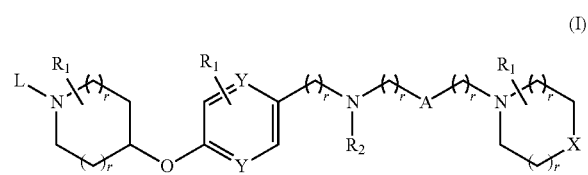

wherein,
at each occurrence, $R_1$ is independently selected from hydrogen, hydroxy, hydroxyalkyl, halogen, alkyl, alkoxy, haloalkyl, haloalkoxy, cyano or —C(O)—NH$_2$;
L is alkyl or

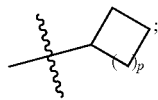

X is C, O or N—$R_2$;
Y is C or N;
A is —C(O)— or —CH$_2$;
$R_2$ is hydrogen, alkyl, —C(O)-alkyl or —S(O)$_2$-alkyl;
"r" is 0 or 1;
"p" is an integer ranging from 0 to 3;or a pharmaceutically acceptable salt thereof.
2. The compound as claimed in claim 1, wherein $R_1$ represents hydrogen, halogen, haloalkyl, hydroxy or alkyl.
3. The compound according to claim 1, which is selected from the group consisting of:
N-[4-(1-Cyclobutyl piperidin-4-yloxy) phenyl]-2-(morpholin-4-yl) acetamide dihydrochloride;
2-[4-(1-Cyclobutyl piperidin-4-yloxy) phenylamino]-1-(morpholin-4-yl) ethanone hydrochloride;
N-[4-(1-Cyclobutyl piperidin-4-yloxy)-2-fluoro-phenyl]-2-(morpholin-4-yl) acetamide dihydrochloride;
N-[4-(1-Cyclobutylpiperidin-4-yloxy) benzyl] morpholine-4-yl amide;
N-[4-(1-Cyclobutyl piperidin-4-yloxy)-3-fluoro phenyl]-2-(morpholin-4-yl) acetamide;
N-[4-(1-Cyclobutyl piperidin-4-yloxy)-2-methyl phenyl]-2-(3,3-difluoro pyrrolidin-l-yl) acetamide;
N-[4-(1-Cyclobutyl piperidin-4-yloxy)-2-trifluoromethyl phenyl]-2-(piperidin-l-yl) acetamide;
N-[4-(1-Cyclopentyl piperidin-4-yloxy) phenyl]-2-(morpholin-4-yl) acetamide;
N-[4-(1-Cyclobutyl piperidin-4-yloxy)-2-trifluoromethyl phenyl]-2-(morpholin-4-yl) acetamide;
N-[4-(1-Isopropyl piperidin-4-yloxy)-2-methyl phenyl]-2-(pyrrolidin-1-yl) acetamide;
N-[4-(1-Cyclobutyl piperidin-4-yloxy)-2-methyl phenyl]-2-(pyrrolidin-l-yl) acetamide;
N-[4-(1-Cyclopentyl piperidin-4-yloxy)-2-methyl phenyl]-2-(piperidin-1-yl) acetamide;
N-[4-(1-Cyclobutyl piperidin-4-yloxy)-2-methyl phenyl]-2-(piperidin-l-yl) acetamide;
N-[4-(1-Cyclobutyl piperidin-4-yloxy) phenyl]-N-methyl-2-(morpholin-4-yl) acetamide;
N-[4-(1-Cyclopentyl piperidin-4-yloxy)-2-methyl phenyl]-2-(R-2-methyl pyrrolidin-l-yl) acetamide;
N-[4-(1-Cyclobutyl piperidin-4-yloxy)-2-methyl phenyl]-2-(R-2-methyl pyrrolidin-l-yl) acetamide;
N-[4-(1-Cyclobutyl piperidin-4-yloxy)-2-methoxy phenyl]-2-(morpholin-4-yl) acetamide;
N-[4-(1-Cyclobutyl piperidin-4-yloxy)-2-trifluoromethyl phenyl]-2-(4-hydroxy piperidin-1-yl) acetamide;
N-[4-(1-Cyclobutyl piperidin-4-yloxy) phenyl]-2-(4-hydroxy piperidin-1-yl) acetamide;
N-[4-(1-Cyclopentyl piperidin-4-yloxy)-2-fluoro phenyl]-2-(morpholin-4-yl) acetamide dihydrochloride;
N-[4-(1-Cyclobutyl piperidin-4-yloxy) phenyl]-2-(pyrrolidin-1-yl) acetamide;
N-[4-(1-Isopropyl piperidin-4-yloxy) phenyl]-2-(morpholin-4-yl) acetamide;
N-[4-(1-Cyclopropyl piperidin-4-yloxy) phenyl]-2-(morpholin-4-yl) acetamide;
N-[4-(1-Cyclobutyl piperidin-4-yloxy) phenyl]-2-(4-isopropyl [1,4] diazepan-1-yl) acetamide;
N-[4-(1-Cyclobutyl piperidin-4-yloxy) phenyl]-2-(2-hydroxymethyl morpholin-4-yl) acetamide;
N-[4-(1-Cyclobutyl piperidin-4-yloxy) phenyl]-3-(morpholin-4-yl) propionamide;
N-[4-(1-Cyclopentyl piperidin-4-yloxy) phenyl]-2-(piperidin-1-yl) acetamide dihydrochloride;
N-[4-(1-Cyclopentyl piperidin-4-yloxy) phenyl]-2-(pyrrolidin-1-yl) acetamide dihydrochloride;
N-[4-(1-Cyclobutyl piperidin-4-yloxy) phenyl]-2-(piperidin-1-yl) acetamide;
N-[4-(1-Cyclobutyl piperidin-4-yloxy)-2-trifluoromethyl phenyl]-2-(pyrrolidin-1-yl) acetamide dihydrochloride;
N-[4-(1-Cyclobutyl piperidin-4-yloxy) phenyl]-N-(2-morpholin-4-yl ethyl) acetamide;
[4-(1-Cyclobutyl piperidin-4-yloxy) phenyl]-(2-morpholin-4-yl ethyl) amine;
N-[4-(1-Cyclobutyl piperidin-4-yloxy) phenyl]-2-(R-2-hydroxymethyl pyrrolidin-1-yl) acetamide L(+) tartarate;
N-[2-(1-Cyclobutyl piperidin-4-yloxy) pyridin-5-yl]-N-[2-(morpholin-4-yl) ethyl] acetamide;
N-[2-(1-Cyclobutyl piperidin-4-yloxy) pyridin-5-yl]-2-(piperidin-1-yl) acetamide;
N-[2-(1-Cyclobutyl piperidin-4-yloxy) pyridin-5-yl]-2-(morpholin-4-yl) acetamide;
N-[4-(1-Cyclobutyl piperidin-4-yloxy)-2-fluoro phenyl]-N-[2-(morpholin-4-yl) ethyl] acetamide;
N-[4-(1-Cyclopropyl piperidin-4-yloxy) phenyl]-N-[2-(morpholin-4-yl) ethyl] acetamide L(+) tartarate;
N-[4-(1-Cyclobutyl piperidin-4-yloxy) phenyl]-2-(1-acetyl piperazin-4-yl) acetamide dihydrochloride;
N-[4-(1-Cyclobutyl piperidine-4-yloxy)-2-methyl phenyl]-2-(4-hydroxy piperidine-1-yl) acetamide;

N-[4-(1-Cyclopropyl piperidin-4-yloxy) phenyl]-2-(R-2-hydroxymethyl pyrrolidin-1-yl) acetamide;
N-[4-(1-Cyclobutyl piperidin-4-yloxy) benzyl]-2-(morpholin-4-yl) acetamide;
N-[4-(1-Cyclobutyl piperidin-4-yloxy)-2-fluoro benzyl]-2-(morpholin-4-yl) acetamide;
N-[4-(1-Cyclobutyl piperidin-4-yloxy) phenyl]-2-(3-hydroxy azetidin-l-yl) acetamide;
N-[4-(1-Cyclobutyl piperidin-4-yloxy)-2-fluoro phenyl]-2-(3-methoxy azetidin-l-yl) acetamide;
N-[4-(1-Cyclobutyl piperidin-4-yloxy)-2-fluoro phenyl]-2-(2-hydroxymethyl pyrrolidin-1-yl) acetamide;
N-[2-Chloro-4-(1-cyclobutyl piperidin-4-yloxy) phenyl]-2-(morpholin-4-yl) acetamide;
N-[2-Chloro-4-(1-cyclobutyl piperidin-4-yloxy) phenyl]-2-(piperidin-1-yl) acetamide;
N-[4-(1-Cyclobutyl piperidin-4-yloxy) phenyl]-2-(tetrahydro pyran-4-yloxy) acetamide;
2-[4-(1-Cyclobutyl piperidin-4-yloxy)-2-fluoro phenylamino]-1-(morpholin-4-yl) ethanone;
N-[4-(1-Cyclobutyl piperidin-4-yloxy)-2-fluoro phenyl]-N-(2-morpholin-4-yl ethyl) acetamide, N-[4-(1-Cyclobutyl piperidin-4-yloxy) phenyl]-2-(morpholin-4-yl) acetamide;
2-[4-(1-Cyclobutyl piperidin-4-yloxy) phenylamino]-1-(morpholin-4-yl) ethanone;
N-[4-(1-Cyclobutyl piperidin-4-yloxy)-2-fluoro-phenyl]-2-(morpholin-4-yl) acetamide;
N-[4-(1-Cyclopentyl piperidin-4-yloxy)-2-fluoro phenyl]-2-(morpholin-4-yl) acetamide;
N-[4-(1-Cyclopentyl piperidin-4-yloxy) phenyl]-2-(piperidin-1-yl) acetamide;
N-[4-(1-Cyclopentyl piperidin-4-yloxy) phenyl]-2-(pyrrolidin-l-yl) acetamide;
N-[4-(1-Cyclobutyl piperidin-4-yloxy)-2-trifluoromethyl phenyl]-2-(pyrrolidin-1-yl) acetamide;
N-[4-(1-Cyclobutyl piperidin-4-yloxy) phenyl]-2-(R-2-hydroxymethyl pyrrolidin-l-yl) acetamide;
N-[4-(1-Cyclopropyl piperidin-4-yloxy) phenyl]-N-[2-(morpholin-4-yl) ethyl] acetamide; and
N-[4-(1-Cyclobutyl piperidin-4-yloxy) phenyl]-2-(1-acetyl piperazin-4-yl) acetamide; or their pharmaceutically acceptable salts.

4. A pharmaceutical composition comprising a compound as claimed in claim 1 and pharmaceutically acceptable excipients.

5. The pharmaceutical composition as claimed in claim 4, for the treatment of clinical conditions mediated through $H_3$ receptor such as cognitive disorders, dementia, attention deficit hyperactivity disorder, schizophrenia, epilepsy, sleep disorders, sleep apnea, obesity, eating disorders and pain in a patient having one or more of said clinical conditions.

6. A process for the preparation of a compound of formula (I) as claimed in claim 1, which comprises the step(s) of:
(a) coupling the compound of formula (1) with compound of formula (2)

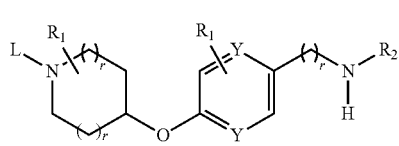

(1)

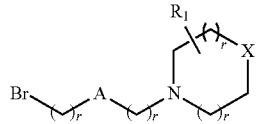

(2)

B=OH, Cl or Br to form a compound of formula (I), wherein all substitutions are as defined in claim 1, (b) optionally converting the compound of formula (I) to their pharmaceutically acceptable salts.

7. A process for the preparation of a compound of formula (I) as claimed in claim 1, which comprises the steps of:
(a) converting the amine compound of formula (1)

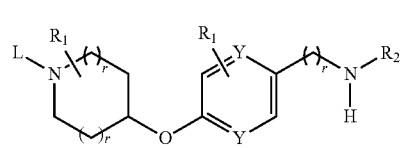

(1)

to the compound of formula (3),

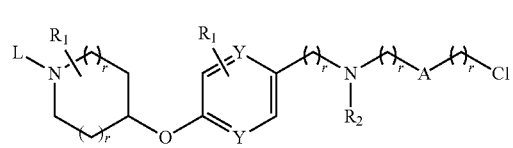

(3)

(b) coupling the compound of formula (3) with compound of formula (4)

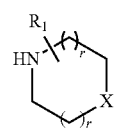

(4)

to form a compound of formula (I), wherein all substitutions are as defined in claim 1, (c) optionally converting the compound of formula (I) to their pharmaceutically acceptable salts.

8. A process for the preparation of a compound of formula (I) as claimed in claim 1, which comprises the steps of:
(a) coupling the compound of formula (5) with compound of formula (4)

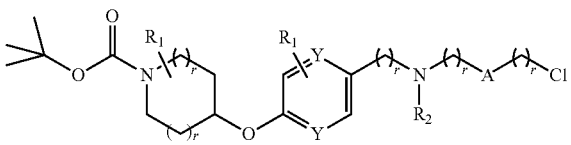

(5)

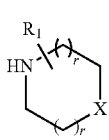

to form a compound of formula (6),

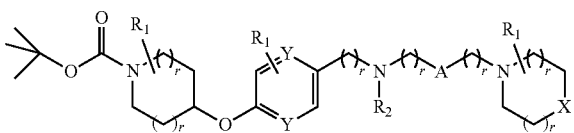

(b) converting the compound of formula (6) to form the compound of formula (I), wherein all substitutions are as defined in claim 1, (c) optionally converting the compound of formula (I) to their pharmaceutically acceptable salts.

9. A method for the treatment of a disorder of the central nervous system related to or affected by the H3 receptor, in a patient having said disorder, which comprises providing to said patient a therapeutically effective amount of a compound of formula (I) as defined in claim 1.

10. The method according to claim 9, wherein said disorder is cognitive disorder, dementia, attention deficit hyperactivity disorder, schizophrenia, epilepsy, sleep disorder, sleep apnea, obesity, eating disorder and/or pain.

11. The compound of formula (I) as claimed in claim 1, for the manufacture of a medicament for treatment of a disorder of central nervous system related to or affected by the H3 receptor in a patient having said disorder.

12. A pharmaceutical composition comprising a compound as claimed in claim 2 and pharmaceutically acceptable excipients.

13. The pharmaceutical composition as claimed in claim 12, for the treatment of clinical conditions mediated through $H_3$ receptor such as cognitive disorders, dementia, attention deficit hyperactivity disorder, schizophrenia, epilepsy, sleep disorders, sleep apnea, obesity, eating disorders and pain in a patient having one or more of said clinical conditions.

14. A pharmaceutical composition comprising a compound as claimed in claim 3 and pharmaceutically acceptable excipients.

15. The pharmaceutical composition as claimed in claim 14, for the treatment of clinical conditions mediated through $H_3$ receptor such as cognitive disorders, dementia, attention deficit hyperactivity disorder, schizophrenia, epilepsy, sleep disorders, sleep apnea, obesity, eating disorders and pain in a patient having one or more of said clinical conditions.

* * * * *